United States Patent
Olesen et al.

(10) Patent No.: US 9,982,287 B2
(45) Date of Patent: May 29, 2018

(54) ENTEROKINASE CLEAVABLE POLYPEPTIDES

(71) Applicant: Novo Nordisk A/S, Bagsvaerd (DK)

(72) Inventors: Kjeld Olesen, Maaloev (DK); Jakob Brandt, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days. days.

(21) Appl. No.: 15/104,793

(22) PCT Filed: Dec. 17, 2014

(86) PCT No.: PCT/EP2014/078165
§ 371 (c)(1),
(2) Date: Jun. 15, 2016

(87) PCT Pub. No.: WO2015/091613
PCT Pub. Date: Jun. 25, 2015

(65) Prior Publication Data
US 2016/0319321 A1 Nov. 3, 2016

(30) Foreign Application Priority Data
Dec. 17, 2013 (EP) ..................................... 13197732

(51) Int. Cl.
| | |
|---|---|
| C07K 1/12 | (2006.01) |
| C07K 14/605 | (2006.01) |
| C12P 21/06 | (2006.01) |
| C12P 21/02 | (2006.01) |
| C07K 7/06 | (2006.01) |
| C07K 14/575 | (2006.01) |
| C07K 14/62 | (2006.01) |

(52) U.S. Cl.
CPC ................ *C12P 21/02* (2013.01); *C07K 1/12* (2013.01); *C07K 7/06* (2013.01); *C07K 14/57563* (2013.01); *C07K 14/605* (2013.01); *C07K 14/62* (2013.01); *C12P 21/06* (2013.01); *C12Y 304/21009* (2013.01); *C07K 2319/00* (2013.01); *C07K 2319/50* (2013.01)

(58) Field of Classification Search
CPC .......... C07K 1/00; C07K 1/12; C07K 14/575; C07K 14/605; C07K 2319/50; C12P 21/02; C12P 21/06; C12Y 304/21009
See application file for complete search history.

(56) References Cited

U.S. PATENT DOCUMENTS 6,906,176 B2 6/2005 Ley et al.
7,648,962 B2 * 1/2010 James .................... C07K 14/58
424/400

FOREIGN PATENT DOCUMENTS

| WO | 01/98366 A2 | 12/2001 |
|---|---|---|
| WO | 2005007699 A2 | 1/2005 |
| WO | 2008/043847 A1 | 4/2008 |

OTHER PUBLICATIONS

Young-Joon Kim et al., "The Pheromone Biosynthesis Activating Neuropeptide (PBAN) Receptor of Heliothis virescens: Identification, Functional Expression, and Structure-Activity Relationships of Ligand Analogs," Peptides, 2008, vol. 29, No. 2, pp. 268-275.
Susanne Neupert et al., "Conservation of the Function Counts: Homologous Neurons Express Sequence-Related Neuropeptides That Originate from Different Genes," Journal of Neurochemistry, 2009, vol. 111, pp. 757-765.
Albert Light, H.S. Savithri, Juris J. Liepnieks, Specificity of bovine enterokinase toward protein substrates, Analytical Biochemistry, vol. 106, Issue 1, Jul. 15, 1980, pp. 199-206.
Boulware K. T. et al., Protease specificity determination by using cellular libraries of peptide substrates (CLiPS), Proceedings of the National Academy of Sciences, 2006, vol. 103, No. 20, 7583-7588.
Database Accession No. X16732, Database EMBL [Online] Nov. 30, 1990, "*P. saccharophila* mta gene encoding maltotetraohydrolase (EC No. = 3.2.1.60)", XP002723748, reterived from http://www.metalife.com/Genbank/45821 on Mar. 27, 2015.
Liew O. W. et al., Preparation of recombinant thioredoxin fused N-terminal proCNP: Analysis of enterokinase cleavage products reveals new enterokinase cleavage sites, Protein Expression and Purification, 2005, vol. 41, 332-340.
Light A, Janska H., Enterokinase (enteropeptidase): comparative aspects, Trends Biochem Sci. Mar. 1989; vol. 14, No. 3, 110-112.
Shahravan S. Hesam et al., Enhancing the specificity of the enterokinase cleavage reaction to promote efficient cleavage of a fusion tag, Protein Expression and Purification, 2008, vol. 59, 314-319.
Viktor Mutt, Kazuhiko Tatemoto, Mats Carlquist, Albert Light, Cleavage of cholecystokinin with enterokinase, Bioscience Reports, Aug. 1981, vol. 1, Issue 8, pp. 651-659.
Yamashina I. The action of enterokinase on trypsinogen, Biochimica et Biophysics Acta, 1956, vol. 20, 433-434.

* cited by examiner

*Primary Examiner* — Jeffrey E. Russel
(74) *Attorney, Agent, or Firm* — Rosemarie R. Wilk-Orescan

(57) ABSTRACT

The present invention relates to Enterokinase-cleavable polypeptides comprising an Enterokinase cleavage site connected to a polypeptide and their use for making the target polypeptide by expression. The invention also relates to DNA sequences, vectors and host cells for use in expressing the Enterokinase-cleavable polypeptides.

10 Claims, No Drawings

ENTEROKINASE CLEAVABLE POLYPEPTIDES

CROSS-REFERENCE TO RELATED APPLICATIONS

This application is a 35 U.S.C. § 371 National Stage application of International Application PCT/EP2014/078165 (WO 2015/091613), filed Dec. 17, 2014, which claims priority to European Patent Application 13197732.4, filed Dec. 17, 2014.

SEQUENCE LISTING

The instant application contains a Sequence Listing which has been submitted in ASCII format via EFS-Web and is hereby incorporated by reference in its entirety. Said ASCII copy, created on Jun. 8, 2016 and amended on Dec. 12, 2017, is named 130043US01SeqList_ST25_corrected_2017.12.12.txt and is 15 KB in size.

BACKGROUND

The techniques of recombinant protein expression allow for the production of large quantities of desirable proteins which may be used for e.g. their biological activity. Such proteins are often expressed as recombinant fusion proteins in microbial host cells.

The protein of interest is often attached to a fusion partner protein or a smaller amino acid extension in order to increase the expression level, facilitate secretion, increase the solubility, promote protein folding, to protect the protein against unintentional proteolysis or to facilitate purification of the protein of interest. The fusion partner protein needs to be removed from the fusion protein by proteolysis to obtain the protein of interest.

One protease used for such processing is enterokinase (E.C. 3.4.21.9). The biologically natural function of this protease is to convert trypsinogen into trypsin by cleavage at a DDDDK processing site (SEQ ID NO: 2, hereafter D4K) in the zymogen (Biochim. Biophys Acta 20 (1956) 443-434).

Similarly, to enable enterokinase catalysed removal of a fusion partner protein a D4K processing site is inserted between the fusion partner protein and the protein of interest. The specificity and efficiency of the enterokinase catalysed processing of the fusion protein is now dependent of e.g. the relative hydrolysis rates of the D4K site and the potential internal degradation sites in the protein of interest. Enterokinase has activity not only for the D4K site but also for quite a number of other sequences, see e.g. Anal. Biochem. 106 (1980) 199-206.

A number of approaches have been used to remedy the disadvantages of enterokinase having limited substrate specificity.

U.S. Pat. No. 6,906,176 describes a number of peptide sequences which are cleaved more efficiently by enterokinase relative to the D4K site.

PNAS 103 (2006) 7583-7588 describes peptide sequences which are cleaved more rapidly by enterokinase than the D4K site.

Protein Expr. Purif. 41 (2005) 332-340 describes a protein comprising the peptide sequence LKGDR (SEQ ID NO: 3) as being more effective than the D4K site for cleavage by enterokinase.

Protein Expr. Purif. 59 (2008) 314-319 describes the enhancement of the specificity of enterokinase cleavage by conducting the cleavage reaction in the presence of urea.

There is a need for more specific enterokinase cleavage reactions for removing a fusion partner protein without cleaving internal sites in the mature protein and without leaving any amino acid extension on the mature protein. Preferably this enterokinase cleavage reaction is well suited for being carried out during an industrial process for manufacture of the matured protein. There is also a need for a more specific enterokinase cleavage reaction which can be used for many different proteins at mild process conditions such that unintended chemical and physical changes to the mature protein do not occur.

SUMMARY

It is an object of the present invention to provide Enterokinase-cleavable fusion polypeptides which comprise an Enterokinase cleavage site which is hydrolysed significantly faster than any secondary cleavage sites which may be present in said Enterokinase-cleavable fusion polypeptides. It is also an object of the present invention to provide Enterokinase-cleavable fusion polypeptides which comprise an Enterokinase cleavage site which is chemically stable.

According to a first aspect of the invention there is provided a method for making a target polypeptide, said method comprising the steps:

a) expressing the Enterokinase-cleavable fusion polypeptide comprising the polypeptide of the formula:

$$Z_2\text{-}X_6\text{-}X_5\text{-}X_4\text{-}G\text{-}D\text{-}R\text{-}Z_1 \qquad \text{(I) SEQ ID NO: 1}$$

wherein
$Z_1$ is a polypeptide comprising at least 2 amino acid residues;
$X_4$ is E, Q, L, D, G, A, S, F, H, Y, W, T or M;
$X_5$ is selected from the genetically encoded amino acids but S and I;
$X_6$ is absent or selected from the genetically encoded amino acids;
$Z_2$ is an optional polypeptide or amino acid residue; wherein said target polypeptide is $Z_1$ in formula (I);

b) contacting said Enterokinase-cleavable polypeptide with an Enterokinase under conditions facilitating cleavage; and c) optionally isolating said target polypeptide.

According to a second aspect of the invention there is provided an enterokinase-cleavable fusion polypeptide comprising the polypeptide of the formula:

$$Z_2\text{-}X_6\text{-}X_5\text{-}X_4\text{-}G\text{-}D\text{-}R\text{-}Z_1 \qquad \text{(I) SEQ ID NO: 1}$$

wherein
$Z_1$ is a polypeptide comprising at least 2 amino acid residues;
$X_4$ is E, Q, L, D, G, A, S, F, H, Y, W, T or M;
$X_5$ is selected from the genetically encoded amino acids but S and I;
$X_6$ is absent or selected from the genetically encoded amino acids; and
$Z_2$ is an optional polypeptide or amino acid residue; and wherein i) $Z_1$ comprises a functional polypeptide, such as a pharmaceutically active polypeptide or an enzyme, or ii) said Enterokinase-cleavable fusion polypeptide consists of formula (I) and $Z_2$ comprises 40 or less amino acid residues, such as $Z_2$ is absent, $Z_2$ is amino acid residue or $Z_2$ is polypeptide comprising 2-40 amino acid residues.

In one embodiment $X_4$ is D. In one embodiment $X_4$ is E. In another embodiment $X_5$-$X_4$ is DE. In another embodiment $X_5$-$X_4$ is DD.

In another embodiment $Z_1$ is a GLP-1 peptide.

According to a third aspect of the invention there is provided a DNA sequence encoding the Enterokinase-cleavable fusion polypeptide according to formula (I).

According to a fourth aspect of the invention there is provided an expression vector comprising the DNA sequence encoding the Enterokinase-cleavable fusion polypeptide according to formula (I), which DNA sequence is operatively linked to an upstream promotor and a downstream terminator.

According to a fifth aspect of the invention there is provided a host cell comprising the expression vector comprising the DNA sequence encoding the Enterokinase-cleavable fusion polypeptide according to formula (I), which DNA sequence is operatively linked to an upstream promotor and a downstream terminator.

DESCRIPTION

In one embodiment the invention relates to an enterokinase-cleavable fusion polypeptide comprising the polypeptide of the formula (I):

$Z_2$-$X_6$-$X_5$-$X_4$-G-D-R-$Z_1$     (I) SEQ ID NO: 1 wherein $Z_1$ is a polypeptide comprising at least 2 amino acid residues;

$X_4$ is E, Q, L, D, G, A, S, F, H, Y, W, T or M;

$X_5$ is selected from the genetically encoded amino acids but S and I;

$X_6$ is absent or selected from the genetically encoded amino acids; and $Z_2$ is an optional polypeptide or amino acid residue. In one embodiment the Enterokinase-cleavable fusion polypeptide consists of formula (I).

The term "Enterokinase" as used herein is intended to mean a pancreatic hydrolase which catalyses the activation by cleavage of trypsinogen into trypsin as part of the catalytic cascade involved in the digestive process. "Enterokinase" includes the native enzyme isolated from any sources as well as the enzyme produced by recombinant expression. One non-limiting example of Enterokinase is the naturally occurring dimer comprising a disulphide-linked heavy chain of approx. 115 kDa and a smaller light chain of approx. 35 kDa. Another non-limiting example of Enterokinase is the light chain alone which comprises the catalytic domain. The light chain alone as well as functional variants thereof has been described to perform well as Enterokinase enzyme, c.f. WO2013/092855A1.

The term "fusion polypeptide" as used herein is intended to mean a polypeptide which comprises two or more polypeptides fused together such as to constitute a non-naturally occurring polypeptide. The size of the polypeptides being fused may vary and depends on the purpose of the fusion polypeptide. Fusion polypeptides are frequently used during the recombinant expression of proteins for reasons of increasing expression, to facilitate the maintenance of a soluble expression product, to facilitate the excretion of the fusion polypeptide or part thereof to the extracellular medium, to protect a polypeptide from being unintentionally processed by proteases or peptidases and the like. In such fusion polypeptides one of the at least two constituent polypeptides is often designated the "target polypeptide" or "mature protein", i.e. being the polypeptide which is to be manufactured by the recombinant expression process.

The term "Enterokinase-cleavable fusion polypeptide" as used herein is intended to mean a fusion polypeptide comprising two polypeptides fused together in each end of an Enterokinase cleavage site such as to constitute a non-naturally occurring polypeptide which under suitable conditions can be cleaved by an Enterokinase at the Enterokinase cleavage site linking the two polypeptides. Thus the Enterokinase-cleavable fusion polypeptide is a non-naturally occurring polypeptide. It is to be understood that each of the two polypeptides comprised by the Enterokinase-cleavable fusion polypeptide may contain secondary sites which are also recognized and cleaved by Enterokinase. However, such secondary cleavage sites will undergo cleavage by Enterokinase at a rate which is lower than the rate at which Enterokinase cleaves the intended cleavage site according to the present invention. In one embodiment all secondary Enterokinase cleavage sites in the Enterokinase-cleavable fusion polypeptide are cleaved by Enterokinase at a rate which is lower than the rate of cleavage of a corresponding D4K site.

In the present context the terms "protein", "polypeptide" and "peptide" may be used interchangeably to designate a polypeptide. It is to be understood that the particular term used has no limitation as to the size of the molecule (unless directly stated in the particular context).

Amino acid residues are designated according to single letter abbreviation according to IUPAC nomenclature, e.g. D meaning aspartic acid (Asp) and G meaning glycine (Gly).

"Genetically encoded amino acids" as used herein is intended to mean the group consisting of the following amino acids: G, P, A, V, L, I, M, C, F, Y, W, H, K, R, Q, N, E, D, S, T as well as any biological modification hereof. In one embodiment amino acids suitable for use in the present invention comprises isosteres of genetically encoded amino acids. Non-limiting examples of such biological modifications are e.g. amidation, glycosylation and disulphide bond formation.

"Analogues" as used herein is intended to mean proteins which are derived from another protein by means of substitution, deletion and/or addition of one or more amino acid residues from the protein. A non-limiting example of analogues of GLP-1(7-37) (SEQ ID NO: 4) are K34R-GLP-1 (7-37) (SEQ ID NO: 5) where residue 34 has been substituted by an arginine residue and K34R-GLP-1(9-37) (SEQ ID NO: 6) where residue 34 has been substituted with an arginine residue and amino acid residues 7-8 have been deleted (using the common numbering of amino acid residues for GLP-1 peptides). In one embodiment GLP-1(7-37) (SEQ ID NO: 4) is HAEGTFTSDVSSYLEGQAAKEFIAWLVKGRG.

"Functional variant" as used herein is intended to mean a chemical variant of a certain protein which retains substantially the same main function as the original protein. Hence a functional variant is typically a modified version of a protein wherein as few modifications are introduced as necessary for the modified protein to obtain some desirable property while preserving substantially the same main function of the original protein. Non-limiting examples of functional variants are e.g. extended proteins, truncated proteins, fusion proteins and analogues. Non-limiting examples of functional variants of bovine Enterokinase light chain are e.g. C112A bovine Enterokinase light chain. A non-limiting example of a functional variant of GLP-1(7-37) is K34R-GLP-1(7-37).

In one embodiment, a functional variant of a protein comprises from 1-2 amino acid substitutions, deletions or additions as compared said protein. In another embodiment, a functional variant comprises from 1-5 amino acid substitutions, deletions or additions as compared to said protein. In another embodiment, a functional variant comprises from 1-15 amino acid substitution, deletion or additions relative to the corresponding naturally occurring protein or naturally occurring sub-sequence of a protein.

In one embodiment $Z_2$ comprises a solubilisation domain. "Solubilisation domain" as used herein is intended to mean a protein which is part of a fusion protein and which is to render said fusion protein more soluble than the fusion partner protein itself under certain conditions. Non-limiting examples of solubilisation domains which may be used as $Z_2$ in formula (I) are DsbC (Thiol:disulfide interchange protein), RL9 (Ribosomal Protein L9) as described in WO2008/043847, MPB (Maltose-binding Protein), NusA (Transcription termination/antitermination protein) and Trx (Thioredoxin).

"Non-naturally occurring polypeptide" as used herein is intended to mean a polypeptide which is not known to occur or does not occur in nature without the intervention of man. A non-limiting example of a non-naturally occurring polypeptide is e.g. a fusion polypeptide where two proteins from different sources are fused together as one polypeptide.

The term "GLP-1 peptide", as used herein, is intended to designate GLP-1 (7-37), GLP-1 (7-36) amide as well as analogues thereof, which are capable of being produced by conventional recombinant DNA techniques as well as conventional synthetic methods. Such GLP-1 peptides include but are not limited to native glucagon-like peptide-1, which may also be referred to as human GLP-1, for instance such peptide fragments which comprises GLP-1 (7-37) and functional variants thereof as disclosed in WO 87/06941; such peptide fragments which comprise GLP-1 (7-36) and functional derivatives thereof as disclosed in WO 90/11296; such analogues of the active GLP-1 peptides 7-34, 7-35, 7-36, and 7-37 as disclosed in WO 91/11457; such N-terminal truncated fragments of GLP-1 as disclosed in EP 0699686-A2; and such GLP-1 analogues and derivatives that include an N-terminal imidazole group as disclosed in EP 0708179-A2. Non-limiting examples of a GLP-1 peptide is GLP-1(7-37), K34R-GLP-1(7-37) and exendin-4(1-39) (SEQ ID NO: 7). In one embodiment exendin-4(1-39) (SEQ ID NO: 7) is HGEGTFTSDLSKQMEEEAVRLFIEWLKNGGPSSGAPPPS.

"Glucagon peptide" as used herein is intended to mean a polypeptide from the preproglucagon family having affinity for the glucagon receptor. Non-limiting examples of a glucagon peptide is glucagon(1-29) (SEQ ID NO: 8) and analogues thereof. In one embodiment glucagon(1-29) (SEQ ID NO: 8) is HSQGTFTSDYSKYLDSRRAQDFVQWLMNT.

"Insulin precursor" as used herein is intended to mean a polypeptide which comprises the A-chain and the B-chain of an insulin and optionally an intervening C-peptide. It is to be understood that the insulin can be human insulin or a functional variant thereof, such as an analogue or a truncated version. A non-limiting example of an insulin precursor is e.g. A(1-21)-AAK-B(1-29)-human insulin (SEQ ID NO: 9). A(1-21)-AAK-B(1-29)-human insulin (SEQ ID NO: 9) is GIVEQCCTSICSLYQLENYCNAAKFVN QHLCGSHLVEALYLVCGERGFFYTPK.

The term "exendin" as used herein, is intended to designate exendin as well as functional variants thereof, including analogues and fragments thereof, e.g. exendin-3 and -4. Exendin as well as analogues and fragments thereof are described in, for example WO 99/43708, the contents of which are herein incorporated by reference in their entirety.

It is preferred that the Enterokinase site in the Enterokinase-cleavable fusion polypeptide be a site which is also robust in terms of chemical stability. Since certain subsequences of amino acid residues in the Enterokinase site are more prone to being less chemically stable, it is generally preferred that the sequence of the Enterokinase site ($X_6$-$X_5$-$X_4$-GDR be one that is chemically stable under the intended conditions.

In the Enterokinase-cleavable fusion polypeptides according to formula (I) $X_4$ is in one embodiment selected from E, Q, L, D, G, A, S, F, H, Y, W or T. In another embodiment $X_4$ is selected from E, Q, L, D, G or A. $X_4$ may be E. $X_4$ may be Q or L. $X_4$ may be D. $X_4$ may be D, G or A. In another embodiment $X_5$ is D or E. In yet another embodiment $X_5$ is D. In one embodiment $X_5$ is not S or I. In one embodiment $X_5$-$X_4$ is selected from the group consisting of DD, DE, DL, DQ, EE, and EQ. In another embodiment $X_5$-$X_4$ is DE or DD. $X_5$-$X_4$ may be DL, DQ or DG. $X_5$-$X_4$ may be DA, DS or EE. $X_5$-$X_4$ may be EQ, EL or ED. $X_5$-$X_4$ may be EG, EA or ES. $X_5$-$X_4$ may be QE, HE, NE or ME. The presence and identity of $X_6$ is lenient. In one embodiment $X_6$ is I, G, L, T, R or S. In another embodiment $X_6$ is absent. $X_6$ may be I, G, L, T, R, S, M, H, F, P, V, W, K, E, Y or Q. $X_6$ may be I, G, L, T, R, S, M, H, F, P, V or W. $X_6$ may be I or G.

In one embodiment $Z_2$ is absent. In another embodiment $Z_2$ is a polypeptide having from 0-10 amino acid residues or having from about 8 to about 200 amino acid residues. Smaller $Z_2$ polypeptides are often used when $Z_2$ is a polypeptide facilitating the expression of the Enterokinase-cleavable fusion polypeptide in a host cell, or when $Z_2$ is to protect a polypeptide being expressed from being proteolytically processed in the N-terminal. In one embodiment $Z_2$ is selected from the group consisting of EEK, EEAEK (SEQ ID NO: 20), HK, EEAHK (SEQ ID NO: 21), E(EA)2HK (SEQ ID NO: 22), E(EA)3HK (SEQ ID NO: 23), EEGHK (SEQ ID NO: 24), EHPK (SEQ ID NO: 63), EEGEPK (SEQ ID NO: 25), EEAHELK (SEQ ID NO: 26), EEAHEVK (SEQ ID NO: 27), EEAHEMK (SEQ ID NO: 28), EEAHEFK (SEQ ID NO: 29), EEAHEYK (SEQ ID NO: 30), EEAHEWKEEGNTTPK (SEQ ID NO: 31) and EELDARLEALK (SEQ ID NO: 32). $Z_2$ may comprise the sequence EEK, EEAEK (SEQ ID NO: 20), or HK. $Z_2$ may comprise the sequence EEAHK (SEQ ID NO: 21), E(EA)2HK (SEQ ID NO: 22) or E(EA)3HK (SEQ ID NO: 23). $Z_2$ may comprise the sequence EEGHK (SEQ ID NO: 24), EHPK (SEQ ID NO: 63) or EEGEPK (SEQ ID NO: 25). $Z_2$ may comprise the sequence EEAHELK (SEQ ID NO: 26), EEAHEVK (SEQ ID NO: 27) or EEAHEMK (SEQ ID NO: 28). $Z_2$ may comprise the sequence EEAHEFK (SEQ ID NO: 29), EEAHEYK (SEQ ID NO: 30), EEAHEWKEEGNTTPK (SEQ ID NO: 31) or EELDARLEALK (SEQ ID NO: 32). In another embodiment $Z_2$ comprises a sequence selected from the group consisting of DV, DVKPGQPLA (SEQ ID NO: 47), DVKPGQPEY (SEQ ID NO: 48), DVKPGEPLY (SEQ ID NO: 49), DVKPGQPLY (SEQ ID NO: 50), DVKPGQPLE (SEQ ID NO: 51) and DVKPGQPMY (SEQ ID NO: 52). In another embodiment $Z_2$ comprises a sequence selected from the group consisting of DVKPGQPLY (SEQ ID NO: 50), DVKPGQELY (SEQ ID NO: 53), DVKPGEPLY (SEQ ID NO: 49), DVKPEQPLY (SEQ ID NO: 54), DVKPGQPEY (SEQ ID NO: 48), DVKEGQPLY (SEQ ID NO: 55), DVKPGQPLA (SEQ ID NO: 47), DVKPGQPLE (SEQ ID NO: 51) and DVEPGQPLY (SEQ ID NO: 64). $Z_2$ may comprise the sequence DVKPGQPLY (SEQ ID NO: 50), DVKPGQELY (SEQ ID NO: 53) or DVKPGEPLY (SEQ ID NO: 49). $Z_2$ may comprise the sequence DVKPEQPLY (SEQ ID NO: 54), DVKPGQPEY (SEQ ID NO: 48), or DVKEGQPLY (SEQ ID NO: 55). $Z_2$ may comprise the sequence DVKPGQPLA (SEQ ID NO: 47), DVKPGQPLE (SEQ ID NO: 51) or DVEPGQPLY (SEQ ID NO: 64). In another embodiment $Z_2$ comprises a sequence selected from the group consisting of QPMYKR (SEQ ID NO: 33), GQPMYK (SEQ ID NO: 34), PGQPMY (SEQ ID NO: 35), KPGQPM (SEQ ID NO: 36), LKPGQP (SEQ ID NO: 37), QLKPGQ (SEQ ID NO: 38), LQLKPG (SEQ ID NO: 39), WLQLKP (SEQ ID NO: 40), HWLQLK (SEQ ID NO: 41), WHWLQL (SEQ ID NO: 42), AWHWLQ (SEQ ID NO: 43), EAWHWL (SEQ ID NO: 44), AEAWHW (SEQ ID NO: 45) and EAEAWH (SEQ ID NO: 46). $Z_2$ may comprise the sequence QPMYKR (SEQ ID NO: 33), GQPMYK (SEQ ID NO: 34) or PGQPMY (SEQ ID NO: 35). $Z_2$ may comprise the sequence KPGQPM (SEQ ID NO: 36), LKPGQP (SEQ ID NO: 37) or QLKPGQ (SEQ ID NO: 38). $Z_2$ may comprise the sequence LQLKPG (SEQ ID NO: 39), WLQLKP (SEQ ID NO: 40) or HWLQLK (SEQ ID NO: 41). $Z_2$ may comprise the sequence WHWLQL (SEQ ID NO: 42), AWHWLQ (SEQ ID NO: 43) or EAWHWL (SEQ ID NO: 44). $Z_2$ may comprise the sequence AEAWHW (SEQ ID NO: 45) or EAEAWH (SEQ ID NO: 46). $Z_2$ may be a polypeptide facilitating the expression of said Enterokinase-cleavable fusion polypeptide in a host cell. In one embodiment $Z_2$ is a polypeptide having from 2 to 50 amino acid residues, such as from 3 to 40, from 4 to 30 or from 5 to 20 amino acid residues. $Z_2$ may be a polypeptide having from 2 to 8 amino acid residues. $Z_2$ may be a polypeptide having at least 8 amino acid residues. $Z_2$ may comprise or consist of 40 or less amino acid residues. $Z_2$ may be a polypeptide having from about 10 to about 25 amino acid residues.

In one embodiment the invention relates to a peptide comprising the amino acid sequence $Z_2$-$X_8$-$X_7$, wherein $Z_2$ is as defined herein; $X_8$ is absent or a peptide comprising an enterokinase cleavage site; and $X_7$ is a polypeptide comprising at least 1 amino acid. In one embodiment $Z_2$ increases recombinant expression of $Z_2$-$X_8$-$X_7$, facilitates maintenance of a soluble expression product $Z_2$-$X_8$-$X_7$, facilitates excretion of $Z_2$-$X_8$-$X_7$ or part thereof to the extracellular medium, protects $X_7$ or part thereof from being unintentionally processed by proteases or peptidases, and/or provides improved properties for capture of $Z_2$-$X_8$-$X_7$ (e.g. by purification by chromatography, such as HPLC). $X_8$ may be absent. $X_8$ may comprise at least 2 amino acids, such as at least 3 amino acids, at least 4 amino acids, or at least 5 amino acids. $X_8$ may comprise 1-30 amino acids, such as 3-20 amino acids, 4-15 amino acids, or at least 5-10 amino acids. $X_7$ may comprise at least 5 amino acids, at least 10 amino acids, or at least 15 amino acids. $X_7$ may comprise 1-100 amino acids, such as 10-70 amino acids or 20-50 amino acids. $X_7$ may be $Z_1$ as defined herein. For example, $Z_1$ may be a GLP-1 peptide or a functional variant thereof. In one embodiment $Z_2$-$X_8$-$X_7$ is an Enterokinase-cleavable fusion polypeptide. $X_8$ may comprise the amino acid sequence $X_6$-$X_5$-$X_4$-G-D-R, wherein $X_6$, $X_5$, and $X_4$ are as defined herein. $X_8$ may comprise the amino acid sequence DDGDR (SEQ ID NO: 56) or DEGDR (SEQ ID NO: 57).

In the Enterokinase-cleavable fusion polypeptides according to formula (I) $Z_1$ is often the target polypeptide to be manufactured by the recombinant expression. In one embodiment $Z_1$ is a pharmaceutically active polypeptide, or a precursor for a pharmaceutically active polypeptide. In an embodiment $Z_1$ is a polypeptide having from about 15 to about 100 amino acid residues. In yet another embodiment $Z_1$ is a polypeptide having from about 15 to about 50 amino acid residues. In another embodiment $Z_1$ is a GLP-1 peptide or a functional variant thereof, such as K34R-GLP-1(7-37) or K34R-GLP-1(9-37). In one embodiment K34R-GLP-1 (7-37) is HAEGTFTSDVSSYLEGQAAKEFIAWLVRGRG (SEQ ID NO: 5). In one embodiment K34R-GLP-1(9-37) is EGTFTSDVSSYLEGQAAKEFIAWLVRGRG (SEQ ID NO: 6). $Z_1$ may comprise the N-terminal sequence HAEGT (SEQ ID NO: 10) or EGTFT (SEQ ID NO: 13). $Z_1$ may comprise the N-terminal sequence HAEGTFTSDVSSYLE (SEQ ID NO: 58), EGTFTSDVSSYLE (SEQ ID NO: 59), or a fragment thereof comprising at least 5 amino acids. In another embodiment $Z_1$ is a glucagon peptide or a functional variant thereof. $Z_1$ may be a glucagon peptide or a functional variant thereof comprising the N-terminal sequence HGTFT (SEQ ID NO: 15). $Z_1$ may be an analogue of GLP-1 (7-37) selected from the group consisting of: (des7-8, 31H, 34Q, 37K); (des7-8, 34R, 37K, 38E); (des7-8, 34R, 37K); (des7-8, 9G, 34R, 37K); (des7-8, 23R, 34R, 37K); (31H, 34Q, 37K); (9Q, 34R, 37K); (30E, 34R, 37K); (34R, 37K, 38G); (34R, 36G, 37K); and (34R, 37K, 38E). $Z_1$ may be an analogue of GLP-1 (7-37) selected from the group consisting of: (i) des7-8, 18K, 34R; (ii) des7-8, 18K, 34Q; (iii) des7-8, 18K, 22E, 34R; (iv) des7-8, 18K, 22E, 34Q; (v) des7-8, 12L, 18K, 34Q; (vi) des7, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26R, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) des7, 18K, 22E, 26R, 34R, 37K; (iixxxx) des7, 18K, 22E, 26R, 27K, 31H, 34G, des35-37; (ixxxx) 7Imp, 18K, 22E, 25V, 26R, 31K, 34G, des35-37; (xxxx) des7-8, 18K, 22E, 25V, 26R, 31K, 34G, des35-37; (xxxxi) 8S, 18K, 22E, 25V, 26R, 31K, 34G, des35-37; (xxxii) des7-8, 18K, 26V, 27K, 34R; (xxxiii) des7-8, 18K, 26H, 30K, 34R, des36-37; (xxxiv) des7-8, 18K, 25V, 26R, 31K, 34R; (xxxv) des7-8, 18K, 22E, 34R, des36-37; (xxxvi) des7-8, 18K, 22E, 26R, 34R, 37K; (xxxvii) des7-8, 18K, 22E, 26R, 31K, 34R; (iixxxxx) des7-8, 18K, 22E, 26R, 31K, 34G, des35-37; (ixxxxx) des7-8, 18K, 22E, 26R, 30K, 34R, des36-37; (xxxxx) des7-8, 18K, 22E, 26R, 30K, 34R; (xxxxxi) des7-8, 18K, 22E, 26R, 27K, 31H, 34R, des36-37; (xxxxxii) des7-8, 18K, 22E, 25V, 26R, 31K, des34-37; (xxxxxiii) des7-8, 18K, 22E, 25V, 26R, 31K, 34R; (xxxxxiv) des7-8, 18K, 22E, 25V, 26R, 31K, 34G, des35-37; (xxxxxv) des7-8, 18K, 22E, 25V, 26R, 30E, 31K, 34G, des35-37; (xxxxxvi) des7-8, 18K, 22E, 25V, 26R, 27L, des35-37; (xxxxxvii) des7-8, 18K, 22E, 25V, 26R, 27K, 34Q; (iixxxxxx) des7-8, 18K, 22E, 25V, 26R, 27K, 31H, 34G, des35-37; (ixxxxxx) des7-8, 18K, 22E, 25V, 26R, 27H, 31K, 34G, des35-37; (xxxxxx) des7-8, 18K, 22E, 25V, 26H, 31K, 34G, des35-37; (xxxxxxi) des7-8, 18K, 22E, 23R, 25V, 26R, 31K, 34G, des35-37; (xxxxxxii) 18K, 22E, 25V, 26R, 27L, 30K, 34G, des35-37; (xxxxxxiii) des7, 18K, 22E, 26R, 27K, 34Q; (xxxxxxiv) 34H; and (xxxxxxv) des7-8, 18K, 34H. $Z_1$ may be an analogue of GLP-1 (7-37) selected from the group consisting of: (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) des7-8, 20K, 22E, 26R, 27K, 30E, 34G, des35-37; (vi) 26R, 27K, 30E, 34R, 36K, 38E; (vii) des7-8, 22K, 25V, 26R, 27K, 31H, 34R; (iix) des7-8, 22K, 25V, 26R, 27K, 34R, des35-37; (ix) des7-8, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) des7-8, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) des7-8, 12K, 22E, 26R, 27K, 31H, 34Q; (ixx) des7-8, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; (xxvi) des7-8, 22E, 24K, 25V, 26R, 27K, 31H, 34Q; and (xxvii) des7-8, 22E, 26R, 27K, 30E, 34R, 36K, 38E, 39G. $Z_1$ may be GLP-1 (7-37) or an analogue of GLP-1 (9-37) selected from the group consisting of (iii) (22E) and (iv) 22E, 30E. $Z_1$ may be an analogue of GLP-1 (9-37) selected from the group consisting of: i) (22E, 26R, 27K, 34R, 38G, 39G, 40G, 41S, 42K); ii) (22E, 26R, 31K, 34R, 38G, 39G, 40G, 41S, 42K); iii) (22E, 26R, 34R, 38K, 39G, 40G, 41S, 42K); iv (22E, 23K, 26R, 34R, 38G, 39G, 40G, 41S, 42K); v) (22E, 26R, 34R, 36K, 38G, 39G, 40G, 41S, 42K); and vi) (18K, 22E, 26R, 34R, 38G, 39G, 40G, 41S, 42K). In yet another embodiment $Z_1$ is an insulin precursor or a functional variant thereof, such as A(1-21)-AAK-B(1-29)-human insulin. In another embodiment $Z_1$ is selected from the group consisting of exendin, PYY, leptin and functional variant thereof.

In one embodiment $Z_1$ and $Z_2$ are derived from different origins, i.e. from different species and/or synthetic origin.

Manufacture of the Fusion Polypeptide

The Enterokinase-cleavable fusion polypeptide may be produced by means of recombinant nucleic acid techniques. In general, nucleic acid sequences encoding $Z_2$, $X_6$-$X_5$-$X_4$-GDR and $Z_1$ are obtained synthetically (for smaller polypeptides) or as cloned DNA modified to encode the desired polypeptide. The nucleic acid sequence encoding $Z_2$ may often be obtained by cloning the wild-type DNA, but when $Z_2$ is a polypeptide of limited size it can also be obtained synthetically. The nucleic acid sequence encoding the Enterokinase site, $X_6$-$X_5$-$X_4$-GDR being a polypeptide of only 5-6 amino acid residues, will usually be obtained synthetically. It may even be encoded by the same nucleic acid sequence encoding $Z_2$, in particular in the situations where $Z_2$ is a rather small polypeptide. The nucleic acid sequences encoding the different parts of $Z_2$, $X_6$-$X_5$-$X_4$-GDR and $Z_1$, are fused in-frame such as to constitute one nucleic acid sequence encoding at least the Enterokinase-cleavable fusion polypeptide of formula (I). Such a fusion polypeptide can be the Enterokinase-cleavable fusion polypeptide, with or without N- or C-terminal extensions (as or within $Z_1$ and $Z_2$) such as a tag or the like, e.g. a His-tag or a solubilisation domain (such as DsbC, RL9, MBP, NusA or Trx). This modified nucleic acid sequence is then inserted into an expression vector, which is in turn transformed or transfected into the expression host cells.

The nucleic acid construct encoding the Enterokinase-cleavable fusion polypeptide may suitably be of genomic, cDNA or synthetic origin. Often, it will comprise nucleic acid sequences having different origins. Amino acid sequence alterations are accomplished by modification of the genetic code by well-known techniques.

In a further aspect the present invention provides a DNA sequence encoding the Enterokinase-cleavable fusion polypeptide of the invention.

The DNA sequence encoding the Enterokinase-cleavable fusion polypeptide is usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the Enterokinase-cleavable fusion polypeptide is operably linked to additional segments required for transcription of the DNA. The term, "operably linked" indicates that the segments are arranged so that they function in concert for their intended purposes, e.g. transcription initiates in a promoter and proceeds through the DNA sequence coding for the polypeptide until it terminates within a terminator.

Thus, expression vectors for use in expressing the Enterokinase-cleavable fusion polypeptide will comprise a promoter capable of initiating and directing the transcription of a cloned gene or cDNA. The promoter may be any DNA sequence, which shows transcriptional activity in the host cell of choice and may be derived from genes encoding proteins either homologous or heterologous to the host cell.

Additionally, expression vectors for expression of the Enterokinase-cleavable fusion polypeptide will also comprise a terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Expression of the Enterokinase-cleavable fusion polypeptide can be aimed for either intracellular expression in the cytosol of the host cell or be directed into the secretory pathway for extracellular expression into the growth medium. Alternatively, expression of the Enterokinase-cleavable fusion polypeptide can be targeted to an organelle.

Intracellular expression is the default pathway and requires an expression vector with a DNA sequence comprising a promoter followed by the DNA sequence encoding the Enterokinase-cleavable fusion polypeptide followed by a terminator.

To direct the Enterokinase-cleavable fusion polypeptide into the secretory pathway of the host cells, a secretory signal sequence (also known as signal peptide or a pre sequence) is needed as an N-terminal extension of the Enterokinase-cleavable fusion polypeptide. A DNA sequence encoding the signal peptide is joined to the 5' end of the DNA sequence encoding the Enterokinase-cleavable fusion polypeptide in the correct reading frame. The signal peptide may be that normally associated with the protein or may be from a gene encoding another secreted protein.

The procedures used to ligate the DNA sequences coding for the Enterokinase-cleavable fusion polypeptide, the promoter, the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

The host cell into which the DNA sequence encoding the Enterokinase-cleavable fusion polypeptide is introduced may be any cell that is capable of expressing the Enterokinase-cleavable fusion polypeptide either intracellularly or extracellularly. If posttranslational modifications are needed, suitable host cells include yeast, fungi, insects and higher eukaryotic cells such as mammalian cells.

Bacterial Expression:

Examples of suitable promoters for directing the transcription of the nucleic acid constructs in a bacterial host cell are, for expression in *E. coli*, the promoters obtained from the lac operon, the trp operon and hybrids thereof trc and tac, all from *E. coli* (DeBoer et al., 1983, *Proceedings of the National Academy of Sciences USA* 80: 21-25). Other even stronger promoters for use in *E. coli* are the bacteriophage promoters from T7 and T5 phages. The T7 promoter requires the presence of the T7 polymerase in the *E. coli* host (Studier and Moffatt, *J. Mol. Biol.* 189, 113, (1986)). All these promoters are regulated by induction with IPTG, lactose or tryptophan to initiate transcription at strategic points in the bacterial growth period. *E. coli* also has strong promoters for continuous expression, e.g. the synthetic promoter used to express hGH in Dalbøge et al, 1987, Biotechnology 5, 161-164.

For the expression in *Bacillus*, the promoters from *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes are suitable examples. Further promoters are described in "Useful proteins from recombinant bacteria" in *Scientific American*, 1980, 242: 74-94; and in Sambrook et al., 1989, supra.

Effective signal peptide coding regions for bacterial host cells are, for *E. coli*, the signal peptides obtained from the genes DegP, OmpA, OmpF, OmpT, PhoA and Enterotoxin STII, all from *E. coli*. For *Bacillus* the signal peptide regions obtained from *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM) and *Bacillus subtilis* prsA. Further signal peptides are described by Simonen and Palva, 1993, *Microbiological Reviews* 57: 109-137. For both *E. coli* and *Bacillus*, signal peptides can be created de novo according to the rules outlined in the algorithm SignalP (Nielsen et al, 1997, Protein Eng. 10, 1-6, Emanuelsen et al, 2007, Nature Protocols 2, 953-971). The signal sequences are adapted to the given context and checked for SignalP score.

Examples of strong terminators for transcription are the aspartase aspA as in the Thiofusion Expression System, the T7 gene 10 terminator in the pET vectors (Studier et al) and the terminators of the ribosomal RNA genes rrnA, rrnD.

In one embodiment the invention relates to a host cell comprising the expression vector comprising the DNA sequence encoding the Enterokinase-cleavable fusion polypeptide according to formula (I). In one embodiment the host cell comprising the expression vector is a yeast, a bacterium or a fungi. In another embodiment the host cell is selected from the group consisting of *Saccharomyces* spp., *Pichia* spp., *Hansenula* spp. and *Kluyveromyces* spp. The host cell may be *Saccharomyces cerevisiae*. In a further embodiment the host cell is selected from the group consisting of *Escherichia coli* and *Bacillus* spp.

Examples of preferred expression hosts are *E. coli* K12 W3110, *E. coli* K12 with a trace of B, MC1061 and *E. coli* B BL21 DE3, harbouring the T7 polymerase by lysogenization with bacteriophage λ. These hosts are selectable with antibiotics when transformed with plasmids for expression. For antibiotics free selection the preferred host is e.g. *E. coli* B BL21 DE3 3xKO with deletion of the 2 D,L-alanine racemase genes Δalr, ΔdadX, and deletion of the Group II capsular gene cluster Δ (kpsM-kpsF), specific for *E. coli* B and often associated with pathogenic behaviour. The deletion of the Group II gene cluster brings *E. coli* B BL21 DE3 3xKO into the same safety category as *E. coli* K12. Selection is based on non-requirement of D-alanine provided by the alr gene inserted in the expression plasmid instead of the AmpR gene.

Once the Enterokinase-cleavable fusion polypeptide has been expressed in a host organism it may be recovered and purified to the required purity by conventional techniques. Non-limiting examples of such conventional recovery and purification techniques are centrifugation, solubilisation, filtration, precipitation, ion-exchange chromatography, immobilized metal affinity chromatography (IMAC), RP-HPLC, gel-filtration and freeze drying.

Examples of recombinant expression and purification of HRV14 3C may be found in e.g. Cordingley et al., 3. Virol. 1989, 63, pp 5037-5045, Birch et al., Protein Expr Purif., 1995, 6, pp 609-618 and in WO2008/043847.

Examples of microbial expression and purification of XaaProDAP from *Lactococcus lactis* may be found in e.g. Chich et al, Anal. Biochem, 1995, 224, pp 245-249 and Xin et al., Protein Expr. Purif. 2002, 24, pp 530-538.

In a further aspect the present invention provides a method for cleaving an Enterokinase-cleavable fusion polypeptide, said method comprising the steps:

a) expressing the Enterokinase-cleavable fusion polypeptide comprising the polypeptide of the formula:

$$Z_2\text{-}X_6\text{-}X_5\text{-}X_4\text{-}G\text{-}D\text{-}R\text{-}Z_1 \qquad \text{(I) SEQ ID NO: 1}$$

wherein $Z_1$ is a polypeptide comprising at least 2 amino acid residues;

$X_4$ is E, Q, L, D, G, A, S, F, H, Y, W, T or M;

$X_5$ is selected from the genetically encoded amino acids but S and I;

$X_6$ is absent or selected from the genetically encoded amino acids;

$Z_2$ is an optional polypeptide or amino acid residue;

wherein said target polypeptide is $Z_1$ in formula (I);

b) contacting said Enterokinase-cleavable fusion polypeptide with an Enterokinase under conditions facilitating cleavage.

In a further aspect the present invention provides a method for making a target polypeptide, said method comprising the steps:

a) expressing the Enterokinase-cleavable fusion polypeptide according to the present invention, wherein said target polypeptide is $Z_1$ in formula (I), b) contacting said Enterokinase-cleavable fusion polypeptide with an Enterokinase under conditions facilitating cleavage, and c) isolating said target polypeptide.

Enterokinases useful for this method are any mammalian Enterokinase, such as bovine Enterokinase, human Enterokinase or functional variants thereof. Enterokinases may also be referred to as enteropeptidases. Since the light chain of Enterokinase comprises the catalytic domain and is active in the absence of the heavy chain, other useful Enterokinases are the bovine light chain or functional variants thereof. Such bovine light chain variants are disclosed in e.g. WO2013/092855A1, e.g. the (C112A) variant and the (C112A, L134K, I135K) variant.

The Enterokinase cleavage according to the above method may be performed under a number of cleavage conditions. In one embodiment the method is conducted wherein the contacting in step b) is carried out in an aqueous solution comprising an organic solvent. This organic solvent may e.g. be selected from methanol, ethanol, i-propanol, n-propanol, acetone, glycerol or a mixture thereof. In one embodiment said organic solvent is ethanol in a concentration from about 10% w/w to about 25% w/w. In one embodiment said organic solvent is methanol, ethanol, i-propanol, n-propanol, acetone, glycerol or a mixture thereof in a concentration from about 10% w/w to about 25% w/w.

EMBODIMENTS OF THE INVENTION

The invention is further described by the following non-limiting embodiments:
1. Enterokinase-cleavable fusion polypeptide comprising the polypeptide of the formula:

$Z_2$-$X_6$-$X_5$-$X_4$-G-D-R-$Z_1$        (I) SEQ ID NO: 1 wherein
    $Z_1$ is a polypeptide comprising at least 2 amino acid residues;
    $X_4$ is E, Q, L, D, G, A, S, F, H, Y, W, T or M;
    $X_5$ is selected from the genetically encoded amino acids but S and I;
    $X_6$ is absent or selected from the genetically encoded amino acids;
    $Z_2$ is an optional polypeptide or amino acid residue.
2. Enterokinase-cleavable fusion polypeptide comprising the polypeptide of the formula:

$Z_2$-$X_6$-$X_5$-$X_4$-G-D-R-$Z_1$        (I) SEQ ID NO: 1 wherein
    $Z_1$ is a polypeptide comprising at least 2 amino acid residues;
    $X_4$ is E, Q, L, D, G, A, S, F, H, Y, W, T or M;
    $X_5$ is selected from the genetically encoded amino acids but S and I;
    $X_6$ is absent or selected from the genetically encoded amino acids;
    $Z_2$ is an optional polypeptide or amino acid residue; and
    wherein i) $Z_1$ comprises a functional polypeptide, such as a pharmaceutically active polypeptide or an enzyme, ii) said Enterokinase-cleavable fusion polypeptide consists of formula (I) and $Z_2$ comprises 40 or less amino acid residues, or iii) $Z_2$ comprises a solubilisation domain.
3. The Enterokinase-cleavable fusion polypeptide according to embodiment 1 or 2, wherein $X_5$ is G, P, A, V, L, M, C, F, Y, W, H, K, R, Q, N, E, D and T.
4. The Enterokinase-cleavable fusion polypeptide according to any of embodiments 1-3, wherein $X_4$ is E, Q, L, D, G, A, S, F, H, Y, W or T.
5. The Enterokinase-cleavable fusion polypeptide according to any of embodiments 1-4, wherein $X_4$ is E, Q, L, D, G or A.
6. The Enterokinase-cleavable fusion polypeptide according to any of embodiments 1-5, wherein $X_4$ is E.
7. The Enterokinase-cleavable fusion polypeptide according to any of embodiments 1-5, wherein $X_4$ is Q.
8. The Enterokinase-cleavable fusion polypeptide according to any of embodiments 1-5, wherein $X_4$ is L.
9. The Enterokinase-cleavable fusion polypeptide according to any of embodiments 1-5, wherein $X_4$ is D.
10. The Enterokinase-cleavable fusion polypeptide according to any of embodiments 1-5, wherein $X_4$ is G.
11. The Enterokinase-cleavable fusion polypeptide according to any of embodiments 1-5, wherein $X_4$ is A.
12. The Enterokinase-cleavable fusion polypeptide according to any of embodiments 1-5, wherein $X_5$ is D or E.
13. The Enterokinase-cleavable fusion polypeptide according to any of embodiments 1-5, wherein $X_5$ is D.
14. The Enterokinase-cleavable fusion polypeptide according to any of embodiments 1-5, wherein $X_5$ is E.
15. The Enterokinase-cleavable fusion polypeptide according to any of embodiments 1-5, wherein $X_5$-$X_4$ is DE.
16. The Enterokinase-cleavable fusion polypeptide according to any of embodiments 1-5, wherein $X_5$-$X_4$ is DD.
17. The Enterokinase-cleavable fusion polypeptide according to any of embodiments 1-5, wherein $X_5$-$X_4$ is DL.
18. The Enterokinase-cleavable fusion polypeptide according to any of embodiments 1-5, wherein $X_5$-$X_4$ is DQ.
19. The Enterokinase-cleavable fusion polypeptide according to any of embodiments 1-5, wherein $X_5$-$X_4$ is DG.
20. The Enterokinase-cleavable fusion polypeptide according to any of embodiments 1-5, wherein $X_5$-$X_4$ is DA.
21. The Enterokinase-cleavable fusion polypeptide according to any of embodiments 1-5, wherein $X_5$-$X_4$ is DS.
22. The Enterokinase-cleavable fusion polypeptide according to any of embodiments 1-5, wherein $X_5$-$X_4$ is EE.
23. The Enterokinase-cleavable fusion polypeptide according to any of embodiments 1-5, wherein $X_5$-$X_4$ is EQ.
24. The Enterokinase-cleavable fusion polypeptide according to any of embodiments 1-5, wherein $X_5$-$X_4$ is EL.
25. The Enterokinase-cleavable fusion polypeptide according to any of embodiments 1-5, wherein $X_5$-$X_4$ is ED.
26. The Enterokinase-cleavable fusion polypeptide according to any of embodiments 1-5, wherein $X_5$-$X_4$ is EG.
27. The Enterokinase-cleavable fusion polypeptide according to any of embodiments 1-5, wherein $X_5$-$X_4$ is EA.
28. The Enterokinase-cleavable fusion polypeptide according to any of embodiments 1-5, wherein $X_5$-$X_4$ is ES.
29. The Enterokinase-cleavable fusion polypeptide according to any of embodiments 1-5, wherein $X_5$-$X_4$ is QE.
30. The Enterokinase-cleavable fusion polypeptide according to any of embodiments 1-5, wherein $X_5$-$X_4$ is HE.
31. The Enterokinase-cleavable fusion polypeptide according to any of embodiments 1-5, wherein $X_5$-$X_4$ is NE.
32. The Enterokinase-cleavable fusion polypeptide according to any of embodiments 1-5, wherein $X_5$-$X_4$ is ME.
33. The Enterokinase-cleavable fusion polypeptide according to any of the preceding embodiments, wherein $X_6$ is I, G, L, T, R, S, M, H, F, P, V, W, K, E, Y or Q.
34. The Enterokinase-cleavable fusion polypeptide according to embodiment 33, wherein $X_6$ is I, G, L, T, R, S, M, H, F, P, V or W.
35. The Enterokinase-cleavable fusion polypeptide according to embodiment 34, wherein $X_6$ is I, G, L, T, R or S.
36. The Enterokinase-cleavable fusion polypeptide according to embodiment 35, wherein $X_6$ is I.
37. The Enterokinase-cleavable fusion polypeptide according to embodiment 35, wherein $X_6$ is G.

38. The Enterokinase-cleavable fusion polypeptide according to any of embodiments 1-32, wherein $X_6$ is absent.
39. The Enterokinase-cleavable fusion polypeptide according to any of the preceding embodiments, wherein $Z_2$ is a polypeptide facilitating the expression of said Enterokinase-cleavable fusion polypeptide in a host cell.
40. The Enterokinase-cleavable fusion polypeptide according to embodiment 39, wherein said host cell is *E. coli*.
41. The Enterokinase-cleavable fusion polypeptide according to embodiment 39, wherein said host cell is a yeast.
42. The Enterokinase-cleavable fusion polypeptide according to embodiments 39-40, wherein said host cell is *Saccharomyces cerevisiae*.
43. The Enterokinase-cleavable fusion polypeptide according to any of the preceding embodiments, wherein $Z_2$ is absent.
44. The Enterokinase-cleavable fusion polypeptide according to any of the preceding embodiments, wherein $Z_2$ is a polypeptide having from 0 to 10 amino acid residues.
45. The Enterokinase-cleavable fusion polypeptide according to any of embodiments 1-42, wherein $Z_2$ is a polypeptide having from 2 to 8 amino acid residues.
46. The Enterokinase-cleavable fusion polypeptide according to any of embodiments 1-42, wherein $Z_2$ is a polypeptide having at least 8 amino acid residues.
47. The Enterokinase-cleavable fusion polypeptide according to any of embodiments 1-42, wherein $Z_2$ comprises 40 or less amino acid residues.
48. The Enterokinase-cleavable fusion polypeptide according any to embodiments claim 1-42, wherein $Z_2$ is an amino acid residue or $Z_2$ is a polypeptide comprising 2-40 amino acid residues.
49. The Enterokinase-cleavable fusion polypeptide according to any of embodiments 1-42, wherein $Z_2$ is a polypeptide having from about 8 to about 200 amino acid residues.
50. The Enterokinase-cleavable fusion polypeptide according to any of embodiments 1-42, wherein $Z_2$ is a polypeptide having from about 10 to about 25 amino acid residues.
51. The Enterokinase-cleavable fusion polypeptide according to any of embodiments 1-42, wherein $Z_2$ is selected from the group consisting of EEK, EEAEK (SEQ ID NO: 20), HK, EEAHK (SEQ ID NO: 21), E(EA)2HK (SEQ ID NO: 22), E(EA)3HK (SEQ ID NO: 23), EEGHK (SEQ ID NO: 24), EHPK (SEQ ID NO: 63), EEGEPK (SEQ ID NO: 25), EEAHELK (SEQ ID NO: 26), EEAHEVK (SEQ ID NO: 27), EEAHEMK (SEQ ID NO: 28), EEAHEFK (SEQ ID NO: 29), EEAHEYK (SEQ ID NO: 30), EEAHEWKEEGNTTPK (SEQ ID NO: 31) and EELDARLEALK (SEQ ID NO: 32).
52. The Enterokinase-cleavable fusion polypeptide according to any of embodiments 1-42, wherein $Z_2$ is selected from the group consisting of DV, DVKPGQPLA (SEQ ID NO: 47), DVKPGQPEY (SEQ ID NO: 48), DVKPGEPLY (SEQ ID NO: 49), DVKPGQPLY (SEQ ID NO: 50), DVKPGQPLE (SEQ ID NO: 51) and DVKPGQPMY (SEQ ID NO: 52).
53. The Enterokinase-cleavable fusion polypeptide according to any of embodiments 1-42, wherein $Z_2$ is selected from the group consisting of DVKPGQPLY (SEQ ID NO: 50), DVKPGQELY (SEQ ID NO: 53), DVKPGEPLY (SEQ ID NO: 49), DVKPEQPLY (SEQ ID NO: 54), DVKPGQPEY (SEQ ID NO: 48), DVKEGQPLY (SEQ ID NO: 55), DVKPGQPLA (SEQ ID NO: 47), DVKPGQPLE (SEQ ID NO: 51) and DVEPGQPLY (SEQ ID NO: 64).
54. The Enterokinase-cleavable fusion polypeptide according to embodiment 1-42, wherein $Z_2$ comprises a sequence selected from the group consisting of QPMYKR (SEQ ID NO: 33), GQPMYK (SEQ ID NO: 34), PGQPMY (SEQ ID NO: 35), KPGQPM (SEQ ID NO: 36), LKPGQP (SEQ ID NO: 37), QLKPGQ (SEQ ID NO: 38), LQLKPG (SEQ ID NO: 39), WLQLKP (SEQ ID NO: 40), HWLQLK (SEQ ID NO: 41), WHWLQL (SEQ ID NO: 42), AWHWLQ (SEQ ID NO: 43), EAWHWL (SEQ ID NO: 44), AEAWHW (SEQ ID NO: 45) and EAEAWH (SEQ ID NO: 46).
55. The Enterokinase-cleavable fusion polypeptide according to any of the preceding embodiments, wherein $Z_2$ comprises a solubilisation domain.
56. The Enterokinase-cleavable fusion polypeptide according to any of the preceding embodiments, wherein $Z_1$ comprises functional polypeptide, such as a pharmaceutically active polypeptide or an enzyme.
57. The Enterokinase-cleavable fusion polypeptide according to any of the preceding embodiments, wherein $Z_1$ is a pharmaceutically active polypeptide, an enzyme, or a precursor hereof.
58. The Enterokinase-cleavable fusion polypeptide according to any of the preceding embodiments, wherein $Z_1$ is a GLP-1 peptide or a functional variant thereof.
59. The Enterokinase-cleavable fusion polypeptide according to embodiment 58, wherein $Z_1$ is K34R-GLP-1(7-37) or K34R-GLP-1(9-37).
60. The Enterokinase-cleavable fusion polypeptide according to any of embodiments 1-57, wherein $Z_1$ is a glucagon peptide or a functional variant thereof.
61. The Enterokinase-cleavable fusion polypeptide according to any of embodiments 1-57, wherein $Z_1$ is an insulin precursor or a functional variant thereof.
62. The Enterokinase-cleavable fusion polypeptide according to any of embodiments 1-57, wherein $Z_1$ is selected from the group consisting of exendin, PYY, leptin and functional variants thereof.
63. The Enterokinase-cleavable fusion polypeptide according to any of the preceding embodiments, wherein $Z_1$ is a polypeptide having from about 15 to about 100 amino acid residues.
64. The Enterokinase-cleavable fusion polypeptide according to any of the preceding embodiments, wherein $Z_1$ is a polypeptide having from about 15 to about 50 amino acid residues.
65. The Enterokinase-cleavable fusion polypeptide according to any of the preceding embodiments, which is a non-naturally occurring polypeptide.
66. The Enterokinase-cleavable fusion polypeptide according to any of the preceding embodiments, wherein $Z_1$ and $Z_2$ are derived from different origins, i.e. different species or synthetic.
67. The Enterokinase-cleavable fusion polypeptide according to any of the preceding embodiments, wherein said Enterokinase-cleavable fusion polypeptide consists of formula (I).
68. DNA sequence encoding the Enterokinase-cleavable fusion polypeptide according to any of embodiments 1-67.
69. Expression vector comprising the DNA sequence according to embodiment 68 operatively linked to an upstream promotor and a downstream terminator.
70. Host cell comprising the expression vector according to embodiment 69.
71. The host cell according to embodiment 70, which is a yeast, a bacterium or a fungi.

72. The host cell according to any of embodiments 70-71, which is selected from the group consisting of *Saccharomyces* spp., *Pichia* spp., *Hansenula* spp. and *Kluyveromyces* spp.

73. The host cell according to any of embodiments 70-72, which is *Saccharomyces cerevisiae*.

74. The host cell according to any of embodiments 70-71, which is selected from the group consisting of *Escherichia coli* and *Bacillus* spp.

75. Method for cleaving an Enterokinase-cleavable fusion polypeptide, said method comprising the steps:
   a) expressing the Enterokinase-cleavable fusion polypeptide comprising the polypeptide of the formula:

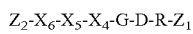  (I) SEQ ID NO: 1 wherein
   $Z_1$ is a polypeptide comprising at least 2 amino acid residues;
   $X_4$ is E, Q, L, D, G, A, S, F, H, Y, W, T or M;
   $X_5$ is selected from the genetically encoded amino acids but S and I;
   $X_6$ is absent or selected from the genetically encoded amino acids;
   $Z_2$ is an optional polypeptide or amino acid residue;
   wherein said target polypeptide is $Z_1$ in formula (I);
   b) contacting said Enterokinase-cleavable fusion polypeptide with an Enterokinase under conditions facilitating cleavage.

76. Method for making a target polypeptide, said method comprising the steps:
   a) expressing the Enterokinase-cleavable fusion polypeptide according to any of embodiments 1-67 wherein said target polypeptide is $Z_1$ in formula (I),
   b) contacting said Enterokinase-cleavable fusion polypeptide with an Enterokinase under conditions facilitating cleavage, and
   c) isolating said target polypeptide.

77. The method according to embodiment 75 or 76, wherein said Enterokinase used in step b) is selected from bovine Enterokinase, the bovine Enterokinase light chain or a functional variant thereof.

78. The method according to any of embodiments 75-78, wherein said Enterokinase is the bovine Enterokinase light chain variant (C112A), (C112A, L134K, I135K) or a functional variant thereof.

79. The method according to any of embodiments 75-77, wherein said contacting in step b) is carried out in an aqueous solution comprising an organic solvent.

80. The method according to embodiment 78, wherein said organic solvent is selected from methanol, ethanol, i-propanol, n-propanol, acetone, glycerol or a mixture thereof.

81. The method according to embodiment 79, wherein said organic solvent is ethanol in a concentration from about 10% w/w to about 25% w/w.

82. The method according to any of embodiments 76-80, wherein said step c) is optional.

83. A peptide comprising the amino acid sequence $Z_2$-$X_8$-$X_7$, wherein $Z_2$ is as defined in any of the preceding embodiments; $X_8$ is absent or a peptide comprising an enterokinase cleavage site; and $X_7$ is a polypeptide comprising at least 1 amino acid.

84. A peptide according to embodiment 83, wherein $X_8$ is absent.

85. A peptide according to embodiment 83, wherein $X_8$ comprises at least 2 amino acids, such as at least 3 amino acids, at least 4 amino acids, or at least 5 amino acids.

86. A peptide according to embodiment 83, wherein $X_8$ comprises 1-30 amino acids, such as 3-20 amino acids, 4-15 amino acids, or at least 5-10 amino acids.

87. A peptide according to any of embodiments 83-86, wherein $X_7$ comprises at least 5 amino acids, at least 10 amino acids, or at least 15 amino acids.

88. A peptide according to any of embodiments 83-86, wherein $X_7$ comprises 1-100 amino acids, such as 10-70 amino acids or 20-50 amino acids.

89. A peptide according to any of embodiments 83-86, wherein $X_7$ is $Z_1$ as defined in any of the preceding embodiments.

90. A peptide according embodiment 89, wherein $Z_1$ is a GLP-1 peptide or a functional variant thereof.

91. A peptide according to any of embodiments 83-90, wherein $Z_2$-$X_8$-$X_7$ is an Enterokinase-cleavable fusion polypeptide.

92. A peptide according to any of embodiments 83-91, wherein $X_8$ comprises the amino acid sequence $X_6$-$X_5$-$X_4$-G-D-R, wherein $X_6$, $X_5$, and $X_4$ are as defined in any of the preceding embodiments.

93. A peptide according to any of embodiments 83-91, wherein $X_8$ comprises the amino acid sequence DDGDR (SEQ ID NO: 56) or DEGDR (SEQ ID NO: 57).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. This invention includes all modifications and equivalents of the subject matter recited in the claims appended hereto as permitted by applicable law.

EXAMPLES

List of Abbreviations

EK: Enterokinase or enterokinase light chain
D4K: DDDDK (SEQ ID NO:2)
NMP: N-Methyl-2-Pyrrolidone.
Abz: 2-aminobenzoyl
Dnp: 2,4-dinitrophenyl
Materials and Methods
General Methods of Preparation
   Method: SPPS_I (Solid Phase Peptide Synthesis)
   Intramolecularly quenched fluorogenic peptide substrates having a C-terminal Lys(Abz)amide fluorophor and a N-terminal Lys(Dnp) quencher, were synthesized by Solid Phase Peptide Synthesis.
   These peptide substrates have the following general structure:

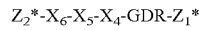  Formula (II)

wherein
X$_6$-X$_5$-X$_4$ have the same meaning as in formula (I) (each being an amino acid, however X$_6$ being optional),
Z$_2$ is Lys(Dnp) and
Z$_1$* is Z$_1$-Lys(Abz)amide, where Z$_1$ is as defined in formula (I).

SPPS_I was performed on a Multipep RSi synthesizer from Intavis Bioanalytical Instruments AG (Koeln, Germany) at 3-µmol scale in parallel using 2.5 fold excess of Fmoc-amino acids (300 mM in NMP with 300 mM Oxyma Pure®) relative to resin loading e.g. Rinkamide-Chematrix (0.5 mmol/g). Fmoc-deprotection was performed using 20% piperidine in NMP. Coupling was performed using 1:1:1:1 amino acid/Oxyma Pure®/DIC/collidine in NMP. All amino acids were "double or triple coupled", meaning that after the first coupling (60 min), the resin is drained and more reagents are added (amino acid, Oxyma Pure®, DIC, and collidine), and the mixture allowed to react again (60 min).

Method: EK Purification
Preparations of purified enterokinase enzyme was prepared according to the procedure described in WO2013/092855A1.

General Methods of Detection and Characterisation
Method: EK-Kinetics_1
EK-kinetics_1 was performed by measuring initial rates of hydrolysis of intramolecularly quenched fluorogenic peptides: Lys(Dnp)-peptide-Lys(Abz)amide according to formula (II). After measuring the background fluorescence of peptides, generally at a substrate concentration in the range of 1 to 50 µM, initial rates of hydrolysis was measured by addition of purified enterokinase enzyme at a concentration enabling reading the initial rate of hydrolysis, i.e. less than 5% hydrolysis in 30 min. Typically an enzyme concentration of 1 to 10 nM may be used. After up to one hour of hydrolysis additional enzyme was added to enable measurement of the fluorescence level at total hydrolysis. Hydrolysis rates were generally measured in 50 mM MOPS buffer, 1 mM EDTA, pH 7.5 at 25° C. using a Perkin Elmer Enspire fluorescence plate reader using 320 nm for excitation and 420 nm for emission.

Method: EK-kinetics_2
EK-kinetics_2 was performed by calculating initial rates of hydrolysis of full length GLP-1 with an N-terminal extension. Substrate concentrations were in the range 150-300 µM. The hydrolysis reaction was started by adding an amount of enterokinase giving a final concentration of 9.5 nM. Samples were taken after 6.2 min, 18.7 min, 43.7 min, 86.3 min, 151.3 min, and 243.8 min and quenched by a 1+9 dilution into 5% acetic acid. A suitable method was used on a Waters iClass UPLC to separate and individually quantify remaining substrate and formed product on an analytical reversed-phase column by integrating peak areas. An equation of the following form was fitted to the raw data:

$$c_{S_t} = c_{S_0} - \frac{k_{cat} * c_E * c_{S_0}}{K_m * \left(1 + \frac{c_{P_t}}{K_i} + c_{S_0}\right)} * t$$

wherein t is time, $c_{S_0}$ is initial substrate concentration, $c_E$ is enzyme concentration, $c_{P_t}$ is product concentration at time t, $c_{S_t}$ is substrate concentration at time t, $k_{cat}$ and $K_m$ are hydrolysis parameters, and $K_i$ is product inhibition constant. A constant $K_i$ of 0.1 µM was used for all reactions. Initial hydrolysis rates were calculated based on the parameters determined for a initial substrate concentration of 1 mg/ml for all peptides. All reactions were performed in 50 mM Tris buffer, 1 mM EDTA, pH 8.5.

Enterokinase Enzymes
The Enterokinase enzymes used for examples herein was the bovine light chain variant (C112A, L134K, I135K) as described in WO2013/092855A1.

Examples 1-39

Relative Cleavage Rate of Enterokinase-Cleavable Fusion Polypeptides Comprising the N-Terminal of GLP-1(7-37).

For all of Examples 1-39 the substrate is Z$_2$*-X$_6$-X$_5$-X$_4$-GDR-Z$_1$*, wherein Z$_1$ is HAEGT (SEQ ID NO: 10), i.e. the N-terminal pentapeptide from GLP-1(7-37), X$_6$ is absent and X$_5$-X$_4$ is as specified in Table 1. The substrates were synthesized by the SPPS-I method and their initial Enterokinase cleavage rates were determined by the EK-kinetics_1 method. The Enterokinase enzymes used for Examples 1-39 was the bovine light chain variant (C112A, L134K, I135K) as described in WO2013/092855A1.

The initial rate of Enterokinase cleavage is normalised against the substrate having a D4K site (replacing the X$_5$-X$_4$-GDR in formula (II)).

For instance, for Example 1 the substrate has the following structure Lys(Dnp)-AEGDR-HAEGT-Lys(Abz)amide (SEQ ID NO: 11) which is a model substrate for Enterokinase-cleavable fusion polypeptides comprising the Enterokinase cleavage site AEGDR (SEQ ID NO: 12).

TABLE 1

Relative Enterokinase cleavage rate of substrates having as Z$_1$ the peptide HAEGT (SEQ ID NO: 10) (D4K site being 100%).

| Example | Z$_1$ | X$_5$-X$_4$ | Activity (%) |
|---|---|---|---|
| 1 | HAEGT (SEQ ID NO: 10) | AE | 382 |
| 2 | HAEGT (SEQ ID NO: 10) | DA | 496 |
| 3 | HAEGT (SEQ ID NO: 10) | DD | 604 |
| 4 | HAEGT (SEQ ID NO: 10) | DD | 601 |
| 5 | HAEGT (SEQ ID NO: 10) | DE | 1096 |
| 6 | HAEGT (SEQ ID NO: 10) | DE | 942 |
| 7 | HAEGT (SEQ ID NO: 10) | DF | 550 |
| 8 | HAEGT (SEQ ID NO: 10) | DG | 431 |
| 9 | HAEGT (SEQ ID NO: 10) | DH | 545 |
| 10 | HAEGT (SEQ ID NO: 10) | DL | 795 |
| 11 | HAEGT (SEQ ID NO: 10) | DL | 722 |
| 12 | HAEGT (SEQ ID NO: 10) | DQ | 770 |
| 13 | HAEGT (SEQ ID NO: 10) | DS | 504 |
| 14 | HAEGT (SEQ ID NO: 10) | DS | 380 |
| 15 | HAEGT (SEQ ID NO: 10) | DT | 434 |
| 16 | HAEGT (SEQ ID NO: 10) | DW | 513 |
| 17 | HAEGT (SEQ ID NO: 10) | DY | 505 |
| 18 | HAEGT (SEQ ID NO: 10) | EA | 582 |
| 19 | HAEGT (SEQ ID NO: 10) | ED | 632 |
| 20 | HAEGT (SEQ ID NO: 10) | EE | 988 |
| 21 | HAEGT (SEQ ID NO: 10) | EF | 486 |
| 22 | HAEGT (SEQ ID NO: 10) | EG | 586 |
| 23 | HAEGT (SEQ ID NO: 10) | EH | 549 |
| 24 | HAEGT (SEQ ID NO: 10) | EL | 659 |
| 25 | HAEGT (SEQ ID NO: 10) | EQ | 808 |
| 26 | HAEGT (SEQ ID NO: 10) | ES | 557 |
| 27 | HAEGT (SEQ ID NO: 10) | ET | 475 |
| 28 | HAEGT (SEQ ID NO: 10) | EW | 456 |
| 29 | HAEGT (SEQ ID NO: 10) | EY | 539 |
| 30 | HAEGT (SEQ ID NO: 10) | FE | 397 |
| 31 | HAEGT (SEQ ID NO: 10) | HE | 468 |
| 32 | HAEGT (SEQ ID NO: 10) | LE | 398 |
| 33 | HAEGT (SEQ ID NO: 10) | ME | 419 |
| 34 | HAEGT (SEQ ID NO: 10) | NE | 457 |

TABLE 1-continued

Relative Enterokinase cleavage rate of substrates having as $Z_1$ the peptide HAEGT (SEQ ID NO: 10) (D4K site being 100%).

| Example | $Z_1$ | $X_5$-$X_4$ | Activity (%) |
|---|---|---|---|
| 35 | HAEGT (SEQ ID NO: 10) | PE | 441 |
| 36 | HAEGT (SEQ ID NO: 10) | QE | 551 |
| 37 | HAEGT (SEQ ID NO: 10) | TE | 393 |
| 38 | HAEGT (SEQ ID NO: 10) | VE | 388 |
| 39 | HAEGT (SEQ ID NO: 10) | YE | 377 |

Examples 40-59

Relative Cleavage Rate of Enterokinase-Cleavable Fusion Polypeptides Comprising the N-Terminal of a GLP-1(9-37) Variant.

For all of the Examples 40-59 the substrate is $Z_2^*$-$X_6$-$X_5$-$X_4$-GDR-$Z_1^*$, wherein $Z_1$ is EGTFT (SEQ ID NO: 13), i.e. the N-terminal pentapeptide from GLP-1(9-37), $X_6$ is absent and $X_5$-$X_4$ is as specified in Table 2. The substrates were synthesized by the SPPS-I method and their initial Enterokinase cleavage rates were determined by the EK-kinetics_1 method. The Enterokinase enzymes used for Examples 40-59 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 2

Relative Enterokinase cleavage rate of substrates having as $Z_1$ the peptide EGTFT (SEQ ID NO: 13) (D4K site being 100%).

| Example | $Z_1$ | $X_5$-$X_4$ | Activity (%) |
|---|---|---|---|
| 40 | EGTFT (SEQ ID NO: 13) | DD | 428 |
| 41 | EGTFT (SEQ ID NO: 13) | DE | 890 |
| 42 | EGTFT (SEQ ID NO: 13) | DF | 419 |
| 43 | EGTFT (SEQ ID NO: 13) | DG | 322 |
| 44 | EGTFT (SEQ ID NO: 13) | DH | 398 |
| 45 | EGTFT (SEQ ID NO: 13) | DL | 438 |
| 46 | EGTFT (SEQ ID NO: 13) | DQ | 412 |
| 47 | EGTFT (SEQ ID NO: 13) | DS | 342 |
| 48 | EGTFT (SEQ ID NO: 13) | DW | 410 |
| 49 | EGTFT (SEQ ID NO: 13) | DY | 373 |
| 50 | EGTFT (SEQ ID NO: 13) | EA | 355 |
| 51 | EGTFT (SEQ ID NO: 13) | ED | 505 |
| 52 | EGTFT (SEQ ID NO: 13) | EE | 580 |
| 53 | EGTFT (SEQ ID NO: 13) | EG | 380 |
| 54 | EGTFT (SEQ ID NO: 13) | EH | 339 |
| 55 | EGTFT (SEQ ID NO: 13) | EL | 396 |
| 56 | EGTFT (SEQ ID NO: 13) | EQ | 442 |
| 57 | EGTFT (SEQ ID NO: 13) | ES | 362 |
| 58 | EGTFT (SEQ ID NO: 13) | EY | 353 |
| 59 | EGTFT (SEQ ID NO: 13) | QE | 411 |

Examples 60-79

Relative Cleavage Rate of Enterokinase-Cleavable Fusion Polypeptides Comprising the N-Terminal of Exendin-4.

For all of the Examples 60-79 the substrate is $Z_2^*$-$X_6$-$X_5$-$X_4$-GDR-$Z_1^*$, wherein $Z_1$ is HGEGT (SEQ ID NO: 14), i.e. the N-terminal pentapeptide from Exendin-4, $X_6$ is absent and $X_5$-$X_4$ is as specified in Table 3. The substrates were synthesized by the SPPS-I method and their initial Enterokinase cleavage rates were determined by the EK-kinetics_1 method. The Enterokinase enzymes used for Examples 60-79 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 3

Relative Enterokinase cleavage rate of substrates having as $Z_1$ the peptide HGEGT (SEQ ID NO: 14) (D4K site being 100%).

| Example | $Z_1$ | $X_5$-$X_4$ | Activity (%) |
|---|---|---|---|
| 60 | HGEGT (SEQ ID NO: 14) | DD | 439 |
| 61 | HGEGT (SEQ ID NO: 14) | DE | 736 |
| 62 | HGEGT (SEQ ID NO: 14) | DF | 253 |
| 63 | HGEGT (SEQ ID NO: 14) | DG | 301 |
| 64 | HGEGT (SEQ ID NO: 14) | DH | 526 |
| 65 | HGEGT (SEQ ID NO: 14) | DL | 438 |
| 66 | HGEGT (SEQ ID NO: 14) | DQ | 467 |
| 67 | HGEGT (SEQ ID NO: 14) | DS | 282 |
| 68 | HGEGT (SEQ ID NO: 14) | DW | 338 |
| 69 | HGEGT (SEQ ID NO: 14) | DY | 469 |
| 70 | HGEGT (SEQ ID NO: 14) | EA | 275 |
| 71 | HGEGT (SEQ ID NO: 14) | ED | 462 |
| 72 | HGEGT (SEQ ID NO: 14) | EE | 641 |
| 73 | HGEGT (SEQ ID NO: 14) | EG | 279 |
| 74 | HGEGT (SEQ ID NO: 14) | EH | 491 |
| 75 | HGEGT (SEQ ID NO: 14) | EL | 502 |
| 76 | HGEGT (SEQ ID NO: 14) | EQ | 432 |
| 77 | HGEGT (SEQ ID NO: 14) | ES | 221 |
| 78 | HGEGT (SEQ ID NO: 14) | EY | 338 |
| 79 | HGEGT (SEQ ID NO: 14) | QE | 275 |

Examples 80-83

Relative Cleavage Rate of Enterokinase-Cleavable Fusion Polypeptides Comprising the N-Terminal of a Glucagon Analogue.

For all of Examples 80-83 the substrate is $Z_2^*$-$X_6$-$X_5$-$X_4$-GDR-$Z_1^*$, wherein $Z_1$ is HGTFT (SEQ ID NO: 15), i.e. the N-terminal pentapeptide from a glucagon analogue, and $X_5$-$X_4$ is as specified in Table 4. The substrates were synthesized by the SPPS-I method, purified by EKpurification and their initial Enterokinase cleavage rates were determined by the EK-kinetics_1 method. The Enterokinase enzymes used for Examples 80-83 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 4

Relative Enterokinase cleavage rate of substrates having as $Z_1$ the peptide HGTFT (SEQ ID NO: 15) (D4K site being 100%).

| Example | $Z_1$ | $X_5$-$X_4$ | Activity (%) |
|---|---|---|---|
| 80 | HGTFT (SEQ ID NO: 15) | DD | 402 |
| 81 | HGTFT (SEQ ID NO: 15) | DE | 392 |
| 82 | HGTFT (SEQ ID NO: 15) | DL | 216 |
| 83 | HGTFT (SEQ ID NO: 15) | DS | 172 |

Examples 84-87

Relative Cleavage Rate of Enterokinase-Cleavable Fusion Polypeptides Comprising the N-Terminal of a Glucagon Analogue.

For all of Examples 84-87 the substrate is $Z_2^*$-$X_6$-$X_5$-$X_4$-GDR-$Z_1^*$, wherein $Z_1$ is QGTFT (SEQ ID NO: 16), i.e. the N-terminal pentapeptide from a glucagon analogue, $X_6$ is absent and $X_5$-$X_4$ is as specified in Table 5. The substrates were synthesized by the SPPS-I method and their initial Enterokinase cleavage rates were determined by the EK-kinetics_1 method. The Enterokinase enzymes used for Examples 84-87 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 5

Relative Enterokinase cleavage rate of substrates having as $Z_1$ the peptide QGTFT (SEQ ID NO: 16) (D4K site being 100%).

| Example | $Z_1$ | $X_5$-$X_4$ | Activity (%) |
|---|---|---|---|
| 84 | QGTFT (SEQ ID NO: 16) | DD | 338 |
| 85 | QGTFT (SEQ ID NO: 16) | DE | 411 |
| 86 | QGTFT (SEQ ID NO: 16) | DL | 222 |
| 87 | QGTFT (SEQ ID NO: 16) | DS | 125 |

Examples 88-91

Relative Cleavage Rate of Enterokinase-Cleavable Fusion Polypeptides Comprising the N-Terminal of Human Glucagon.

For all of Examples 88-91 the substrate is $Z_2$*-$X_6$-$X_5$-$X_4$-GDR-$Z_1$*, wherein $Z_1$ is HSQGT (SEQ ID NO: 17), i.e. the N-terminal pentapeptide from human glucagon, $X_6$ is absent and $X_5$-$X_4$ is as specified in Table 6. The substrates were synthesized by the SPPS-I method and their initial Enterokinase cleavage rates were determined by the EK-kinetics_1 method. The Enterokinase enzymes used for Examples 88-91 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 6

Relative Enterokinase cleavage rate of substrates having as $Z_1$ the peptide HSQGT (SEQ ID NO: 17) (D4K site being 100%).

| Example | $Z_1$ | $X_5$-$X_4$ | Activity (%) |
|---|---|---|---|
| 88 | HSQGT (SEQ ID NO: 17) | DD | 310 |
| 89 | HSQGT (SEQ ID NO: 17) | DE | 621 |
| 90 | HSQGT (SEQ ID NO: 17) | DL | 268 |
| 91 | HSQGT (SEQ ID NO: 17) | DS | 200 |

Examples 92-110

Relative Cleavage Rate of Reference Enterokinase-Cleavable Fusion Polypeptides Comprising the N-Terminal of GLP-1(7-37) and Different $X_6$.

For all of Examples 92-110 the substrate is $Z_2$*-$X_6$-$X_5$-$X_4$-GDR-$Z_1$*, wherein $Z_1$ is HAEGT (SEQ ID NO: 10), i.e. the N-terminal pentapeptide from GLP-1(7-37), $X_5$-$X_4$ is DE and $X_6$ is as specified in Table 7. The substrates were synthesized by the SPPS-I method and their initial Enterokinase cleavage rates were determined by the EK-kinetics_1 method. The Enterokinase enzymes used for Examples 92-110 was the bovine light chain variant (C112A, L134K, I135K) as described in WO2013/092855A1.

The initial rate of Enterokinase cleavage is normalised against the substrate having $X_6$-$X_5$-$X_4$=ADE (100%).

TABLE 7

Relative Enterokinase cleavage rate of substrates having as $Z_1$ the peptide HAEGT (SEQ ID NO: 10), $X_6$ as specified in the table and $X_5$-$X_4$ = DE ($X_6$-$X_5$-$X_4$ = ADE being 100%).

| Example | $Z_1$ | $X_6$-$X_5$-$X_4$ | Activity (%) |
|---|---|---|---|
| 92 | HAEGT (SEQ ID NO: 10) | ADE | 100 |
| 93 | HAEGT (SEQ ID NO: 10) | DDE | 113 |
| 94 | HAEGT (SEQ ID NO: 10) | EDE | 159 |
| 95 | HAEGT (SEQ ID NO: 10) | FDE | 200 |
| 96 | HAEGT (SEQ ID NO: 10) | GDE | 267 |
| 97 | HAEGT (SEQ ID NO: 10) | HDE | 204 |
| 98 | HAEGT (SEQ ID NO: 10) | IDE | 283 |
| 99 | HAEGT (SEQ ID NO: 10) | KDE | 175 |
| 100 | HAEGT (SEQ ID NO: 10) | LDE | 259 |
| 101 | HAEGT (SEQ ID NO: 10) | MDE | 209 |
| 102 | HAEGT (SEQ ID NO: 10) | NED | 114 |
| 103 | HAEGT (SEQ ID NO: 10) | PDE | 194 |
| 104 | HAEGT (SEQ ID NO: 10) | QDE | 141 |
| 105 | HAEGT (SEQ ID NO: 10) | RDE | 222 |
| 106 | HAEGT (SEQ ID NO: 10) | SDE | 222 |
| 107 | HAEGT (SEQ ID NO: 10) | TDE | 237 |
| 108 | HAEGT (SEQ ID NO: 10) | VDE | 184 |
| 109 | HAEGT (SEQ ID NO: 10) | WDE | 181 |
| 110 | HAEGT (SEQ ID NO: 10) | YDE | 153 |

Examples 111-117

Relative Cleavage Rate of Reference Enterokinase-Cleavable Fusion Polypeptides Comprising the N-Terminal of GLP-1(7-37).

For all of the Examples 111-117 the substrate is $Z_2$*-$X_6$-$X_5$-$X_4$-GDR-$Z_1$*, wherein $Z_1$ is HAEGT (SEQ ID NO: 10), i.e. the N-terminal pentapeptide from GLP-1(7-37), $X_6$ is absent and the Enterokinase site corresponding to $X_5$-$X_4$-GDR is as specified in Table 8. The substrates were synthesized by the SPPS-I method and their initial Enterokinase cleavage rates were determined by the EK-kinetics_1 method.

The EK-site as specified in Table 8 designates the pentapeptide corresponding to the $X_5$-$X_4$-GDR sequence. Hence, in Example 111 the substrate has the structure Lys(Dnp)-IMGDRHAEGT-Lys(Abz)amide (SEQ ID NO: 18), and in Example 112 the substrate has the structure Lys(Dnp)-INDDRHAEGT-Lys(Abz)amide (SEQ ID NO: 19). Thus, in Example 112 the Enterokinase site does not include the GDR sequence but rather a DDR sequence. The Enterokinase enzymes used for Examples 111-117 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 8

Relative Enterokinase cleavage rate of reference substrates having as $Z_1$ the peptide HAEGT (SEQ ID NO: 10) (D4K site being 100%).

| Example | $Z_1$ | EK-site (corresponding to $X_5$-$X_4$-GDR) | Activity (%) |
|---|---|---|---|
| 111 | HAEGT (SEQ ID NO: 10) | IMGDR | 125 |
| 112 | HAEGT (SEQ ID NO: 10) | INDDR | 126 |
| 113 | HAEGT (SEQ ID NO: 10) | IYGDR | 117 |
| 114 | HAEGT (SEQ ID NO: 10) | NYTDR | 59 |
| 115 | HAEGT (SEQ ID NO: 10) | SGGDR | 243 |
| 116 | HAEGT (SEQ ID NO: 10) | SSGDR | 191 |
| 117 | HAEGT (SEQ ID NO: 10) | VIGDR | 68 |

Examples 118-137

Relative Cleavage Rate of Enterokinase-Cleavable Fusion Polypeptides Comprising the Entire [Arg34]GLP-1(9-37) Sequence and an N-Terminal Extension and Reference Enterokinase-Cleavable Fusion Polypeptides Comprising DDDDK (SEQ ID NO: 2).

For all of the Examples 118-135 the substrate was $Z_2^*$-$X_6$-$X_5$-$X_4$-GDR-$Z_1^*$ (SEQ ID NO: 60), wherein $Z_2$ and $Z_1$ are as defined in Table 9, i.e. $Z_2$ is an N-terminal extension of the Enterokinase-cleavable fusion polypeptide and $Z_1$ is [Arg34]GLP-1(9-37), $X_6$ is absent and the Enterokinase site corresponding to $X_5$-$X_4$-GDR is as specified in Table 9; except in reference examples, and as specified in Table 9 (e.g. Example 118), the substrate was $Z_2^*$-$X_6$-DDDDK-$Z_1^*$ (SEQ ID NO: 61). The substrates were synthesized by the SPPS-I method and their initial Enterokinase cleavage rates were determined by the EK-kinetics_2 method.

The EK-site as specified in Table 9 designates the penta-peptide corresponding to the $X_5$-$X_4$-GDR sequence. Hence, in Example 119 the substrate has the structure DVKPGQ-PLYDEGDR-[Arg34]GLP-1(9-37) (SEQ ID NO: 62).

The Enterokinase enzymes used for Examples 118-135 was the bovine light chain variant (C112A, L134K, I135K) as described in WO2013/092855A1.

The initial rate of Enterokinase cleavage is normalised against the substrate having a D4K site (replacing the $X_5$-$X_4$-GDR in formula (II)).

TABLE 9

Relative Enterokinase cleavage rate of reference substrates comprising the entire [Arg34]GLP-1(9-37) sequence as Z1 and an N-terminal extension as $Z_2$ as defined below (slowest D4K site in this set being 100%).

| Example | $Z_2$ | $Z_1$ | EK-site (corresponding to $X_5$-$X_4$-GDR) | Activity (%) |
|---|---|---|---|---|
| 118 | DVKPGQPLY | [Arg34]GLP-1(9-37) | DDDDK (SEQ ID NO: 2) | 136 |
| 119 | (SEQ ID NO: 50) | | DEGDR (SEQ ID NO: 57) | 707 |
| 120 | DVKPGQELY | [Arg34]GLP-1(9-37) | DDDDK (SEQ ID NO: 2) | 168 |
| 121 | (SEQ ID NO: 53) | | DEGDR (SEQ ID NO: 57) | 1039 |
| 122 | DVKPGEPLY | [Arg34]GLP-1(9-37) | DDDDK (SEQ ID NO: 2) | 162 |
| 123 | (SEQ ID NO: 49) | | DEGDR (SEQ ID NO: 57) | 895 |
| 124 | DVKPEQPLY | [Arg34]GLP-1(9-37) | DDDDK (SEQ ID NO: 2) | 167 |
| 125 | (SEQ ID NO: 54) | | DEGDR (SEQ ID NO: 57) | 803 |
| 126 | DVKPGQPEY | [Arg34]GLP-1(9-37) | DDDDK (SEQ ID NO: 2) | 158 |
| 127 | (SEQ ID NO: 48) | | DEGDR (SEQ ID NO: 57) | 625 |
| 128 | DVKEGQPLY | [Arg34]GLP-1(9-37) | DDDDK (SEQ ID NO: 2) | 178 |
| 129 | (SEQ ID NO: 55) | | DEGDR (SEQ ID NO: 57) | 913 |
| 130 | DVKPGQPLA | [Arg34]GLP-1(9-37) | DDDDK (SEQ ID NO: 2) | 134 |
| 131 | (SEQ ID NO: 47) | | DEGDR (SEQ ID NO: 57) | 476 |
| 132 | DVKPGQPLE | [Arg34]GLP-1(9-37) | DDDDK (SEQ ID NO: 2) | 100 |
| 133 | (SEQ ID NO: 51) | | DEGDR (SEQ ID NO: 57) | 653 |
| 134 | DVEPGQPLY | [Arg34]GLP-1(9-37) | DDDDK (SEQ ID NO: 2) | 203 |
| 135 | (SEQ ID NO: 64) | | DEGDR (SEQ ID NO: 57) | 951 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for making a target polypeptide, said method comprising the steps:
   a) expressing an enterokinase-cleavable fusion polypeptide comprising a polypeptide of formula I:

$Z_2$-$X_6$-$X_5$-$X_4$-G-D-R-$Z_1$     (I) SEQ ID NO: 1 wherein $Z_1$ is a polypeptide comprising at least 2 amino acid residues;

$X_4$ is an amino acid selected from the group consisting of E, Q, L, D, G, A, S, F, H, Y, W, T and M;

$X_5$ is an amino acid selected from the group consisting of genetically encoded amino acids other than S and I;

$X_6$ is absent or an amino acid selected from the group consisting of genetically encoded amino acids;

$Z_2$ is optionally a polypeptide or an amino acid residue; wherein said target polypeptide is $Z_1$ in formula (I);

b) contacting said enterokinase-cleavable fusion polypeptide with an enterokinase under conditions facilitating cleavage of said fusion polypeptide; and c) optionally isolating said target polypeptide from said cleavage reaction in b).

2. The method according to claim 1, wherein $X_4$ is E, Q, L, D, G or A.

3. The method according to claim 2, wherein $X_5$-$X_4$ is selected from the group consisting of DD, DE, DL, DQ, EE, and EQ.

4. The method according to claim 3, wherein $X_5$-$X_4$ is DD or DE.

5. The method according to claim 1, wherein $Z_2$ is a polypeptide facilitating the expression of said enterokinase-cleavable fusion polypeptide in a host cell.

6. The method according to claim 1, wherein $Z_2$ is a polypeptide having from 2 to 50 amino acid residues, $Z_2$ is an amino acid residue, or $Z_2$ is absent.

7. The method according to claim 1, wherein $Z_1$ comprises a pharmaceutically active polypeptide or an enzyme.

8. The method according to claim 7, wherein $Z_1$ is a GLP-1 peptide or a functional variant thereof.

9. The method according to claim 7, wherein $Z_1$ is a glucagon peptide or a functional variant thereof.

10. The method according to claim 1, wherein said contacting in step b) is carried out in an aqueous solution comprising an organic solvent.

\* \* \* \* \*

SEQUENCE LISTING

<160> NUMBER OF SEQ ID NOS: 64

<210> SEQ ID NO 1
<211> LENGTH: 9
<212> TYPE: PRT
<213> ORGANISM: ARTIFICIAL
<220> FEATURE:
<223> OTHER INFORMATION: Enterokinase cleavable fusionpolypeptide of Formula (I)
<220> FEATURE:
<221> NAME/KEY: MISC_FEATURE

```
<222> LOCATION: (1)..(1)
<223> OTHER INFORMATION: Optional polypeptide or amino acid residue
<220> FEATURE:
<221> NAME/KEY: MISC_FEATURE
<222> LOCATION: (2)..(2)
<223> OTHER INFORMATION: Optional amino acid residue selected from the
      genetically encoded amino acids
<220> FEATURE:
<221> NAME/KEY: MISC_FEATURE
<222> LOCATION: (3)..(3)
<223> OTHER INFORMATION: Optional amino acid residue selected from the
      genetically encoded amino acids but not S and I
<220> FEATURE:
<221> NAME/KEY: MISC_FEATURE
<222> LOCATION: (4)..(4)
<223> OTHER INFORMATION: Amino acid residue selected from E, Q, L, D,
      G, A, S, F, H, Y, W, T and M
<220> FEATURE:
<221> NAME/KEY: MISC_FEATURE
<222> LOCATION: (8)..(8)
<223> OTHER INFORMATION: Amino acid residue which is part of a
      polypeptide comprising at least 2 amino acid residues, said
      polypeptide indicated here by Xaa8-Xaa9
<220> FEATURE:
<221> NAME/KEY: MISC_FEATURE
<222> LOCATION: (9)..(9)
<223> OTHER INFORMATION: Amino acid residue which is part of a
      polypeptide comprising at least 2 amino acid residues, said
      polypeptide indicated here by Xaa8-Xaa9

<400> SEQUENCE: 1

Xaa Xaa Xaa Xaa Gly Asp Arg Xaa Xaa
1               5

<210> SEQ ID NO 2
<211> LENGTH: 5
<212> TYPE: PRT
<213> ORGANISM: Homo sapiens

<400> SEQUENCE: 2

Asp Asp Asp Asp Lys
1               5

<210> SEQ ID NO 3
<211> LENGTH: 5
<212> TYPE: PRT
<213> ORGANISM: ARTIFICIAL
<220> FEATURE:
<223> OTHER INFORMATION: Synthetic Enterokinase cleavage site

<400> SEQUENCE: 3

Leu Lys Gly Asp Arg
1               5

<210> SEQ ID NO 4
<211> LENGTH: 31
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 31
<212> TYPE: PRT
<213> ORGANISM: ARTIFICIAL
<220> FEATURE:
```

```
<223> OTHER INFORMATION: Analogue of GLP-1(7-37)

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 6
<211> LENGTH: 29
<212> TYPE: PRT
<213> ORGANISM: ARTIFICIAL
<220> FEATURE:
<223> OTHER INFORMATION: Analogue of GLP-1(9-37)

<400> SEQUENCE: 6

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 7
<211> LENGTH: 39
<212> TYPE: PRT
<213> ORGANISM: Heloderma suspectum

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 29
<212> TYPE: PRT
<213> ORGANISM: Homo sapiens

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 9
<211> LENGTH: 53
<212> TYPE: PRT
<213> ORGANISM: ARTIFICIAL
<220> FEATURE:
<223> OTHER INFORMATION: Insulin precursor comprising A(1-21), B(1-29)
      and an AAK C-peptide

<400> SEQUENCE: 9

Gly Ile Val Glu Gln Cys Cys Thr Ser Ile Cys Ser Leu Tyr Gln Leu
1               5                   10                  15

Glu Asn Tyr Cys Asn Ala Ala Lys Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys
        50
```

```
<210> SEQ ID NO 10
<211> LENGTH: 5
<212> TYPE: PRT
<213> ORGANISM: ARTIFICIAL
<220> FEATURE:
<223> OTHER INFORMATION: N-terminal of GLP-1(7-37)

<400> SEQUENCE: 10

His Ala Glu Gly Thr
1               5

<210> SEQ ID NO 11
<211> LENGTH: 12
<212> TYPE: PRT
<213> ORGANISM: ARTIFICIAL
<220> FEATURE:
<223> OTHER INFORMATION: Synthetic peptide substrate for Enterokinase
<220> FEATURE:
<221> NAME/KEY: MISC_FEATURE
<222> LOCATION: (1)..(1)
<223> OTHER INFORMATION: Lysine(2,4-dinitrophenyl)
<220> FEATURE:
<221> NAME/KEY: MISC_FEATURE
<222> LOCATION: (12)..(12)
<223> OTHER INFORMATION: Lysine(2-aminobenzoyl)amide

<400> SEQUENCE: 11

Xaa Ala Glu Gly Asp Arg His Ala Glu Gly Thr Xaa
1               5                   10

<210> SEQ ID NO 12
<211> LENGTH: 5
<212> TYPE: PRT
<213> ORGANISM: ARTIFICIAL
<220> FEATURE:
<223> OTHER INFORMATION: Synthetic Enterokinase cleavage site

<400> SEQUENCE: 12

Ala Glu Gly Asp Arg
1               5

<210> SEQ ID NO 13
<211> LENGTH: 5
<212> TYPE: PRT
<213> ORGANISM: ARTIFICIAL
<220> FEATURE:
<223> OTHER INFORMATION: N-terminal of a GLP-1(9-37) analogue

<400> SEQUENCE: 13

Glu Gly Thr Phe Thr
1               5

<210> SEQ ID NO 14
<211> LENGTH: 5
<212> TYPE: PRT
<213> ORGANISM: ARTIFICIAL
<220> FEATURE:
<223> OTHER INFORMATION: N-terminal of Exendin-4

<400> SEQUENCE: 14

His Gly Glu Gly Thr
1               5

<210> SEQ ID NO 15
<211> LENGTH: 5
<212> TYPE: PRT
<213> ORGANISM: ARTIFICIAL
```

```
<220> FEATURE:
<223> OTHER INFORMATION: N-terminal of a glucagon analogue

<400> SEQUENCE: 15

His Gly Thr Phe Thr
1               5

<210> SEQ ID NO 16
<211> LENGTH: 5
<212> TYPE: PRT
<213> ORGANISM: ARTIFICIAL
<220> FEATURE:
<223> OTHER INFORMATION: N-terminal of a glucagon analogue

<400> SEQUENCE: 16

Gln Gly Thr Phe Thr
1               5

<210> SEQ ID NO 17
<211> LENGTH: 5
<212> TYPE: PRT
<213> ORGANISM: ARTIFICIAL
<220> FEATURE:
<223> OTHER INFORMATION: N-terminal of a glucagon analogue

<400> SEQUENCE: 17

His Ser Gln Gly Thr
1               5

<210> SEQ ID NO 18
<211> LENGTH: 12
<212> TYPE: PRT
<213> ORGANISM: ARTIFICIAL
<220> FEATURE:
<223> OTHER INFORMATION: Synthetic peptide substrate for Enterokinase
<220> FEATURE:
<221> NAME/KEY: MISC_FEATURE
<222> LOCATION: (1)..(1)
<223> OTHER INFORMATION: Lysine(2,4-dinitro-phenyl)
<220> FEATURE:
<221> NAME/KEY: MISC_FEATURE
<222> LOCATION: (12)..(12)
<223> OTHER INFORMATION: Lysine(2-aminobenzoyl)amide

<400> SEQUENCE: 18

Xaa Ile Met Gly Asp Arg His Ala Glu Gly Thr Xaa
1               5                   10

<210> SEQ ID NO 19
<211> LENGTH: 12
<212> TYPE: PRT
<213> ORGANISM: ARTIFICIAL
<220> FEATURE:
<223> OTHER INFORMATION: Synthetic peptide substrate for Enterokinase
<220> FEATURE:
<221> NAME/KEY: MISC_FEATURE
<222> LOCATION: (1)..(1)
<223> OTHER INFORMATION: Lysine(2,4-dinitrophenyl)
<220> FEATURE:
<221> NAME/KEY: MISC_FEATURE
<222> LOCATION: (12)..(12)
<223> OTHER INFORMATION: Lysine(2-aminobenzoyl)amide

<400> SEQUENCE: 19

Xaa Ile Asn Asp Asp Arg His Ala Glu Gly Thr Xaa
1               5                   10

<210> SEQ ID NO 20
<211> LENGTH: 5
```

```
<212> TYPE: PRT
<213> ORGANISM: ARTIFICIAL
<220> FEATURE:
<223> OTHER INFORMATION: Z2 sequence

<400> SEQUENCE: 20

Glu Glu Ala Glu Lys
1               5

<210> SEQ ID NO 21
<211> LENGTH: 5
<212> TYPE: PRT
<213> ORGANISM: ARTIFICIAL
<220> FEATURE:
<223> OTHER INFORMATION: Z2 sequence

<400> SEQUENCE: 21

Glu Glu Ala His Lys
1               5

<210> SEQ ID NO 22
<211> LENGTH: 7
<212> TYPE: PRT
<213> ORGANISM: ARTIFICIAL
<220> FEATURE:
<223> OTHER INFORMATION: Z2 sequence

<400> SEQUENCE: 22

Glu Glu Ala Glu Ala His Lys
1               5

<210> SEQ ID NO 23
<211> LENGTH: 9
<212> TYPE: PRT
<213> ORGANISM: ARTIFICIAL
<220> FEATURE:
<223> OTHER INFORMATION: Z2 sequence

<400> SEQUENCE: 23

Glu Glu Ala Glu Ala Glu Ala His Lys
1               5

<210> SEQ ID NO 24
<211> LENGTH: 5
<212> TYPE: PRT
<213> ORGANISM: ARTIFICIAL
<220> FEATURE:
<223> OTHER INFORMATION: Z2 sequence

<400> SEQUENCE: 24

Glu Glu Gly His Lys
1               5

<210> SEQ ID NO 25
<211> LENGTH: 6
<212> TYPE: PRT
<213> ORGANISM: ARTIFICIAL
<220> FEATURE:
<223> OTHER INFORMATION: Z2 sequence

<400> SEQUENCE: 25

Glu Glu Gly Glu Pro Lys
1               5

<210> SEQ ID NO 26
<211> LENGTH: 7
<212> TYPE: PRT
```

```
<213> ORGANISM: ARTIFICIAL
<220> FEATURE:
<223> OTHER INFORMATION: Z2 sequence

<400> SEQUENCE: 26

Glu Glu Ala His Glu Leu Lys
1               5

<210> SEQ ID NO 27
<211> LENGTH: 7
<212> TYPE: PRT
<213> ORGANISM: ARTIFICIAL
<220> FEATURE:
<223> OTHER INFORMATION: Z2 sequence

<400> SEQUENCE: 27

Glu Glu Ala His Glu Val Lys
1               5

<210> SEQ ID NO 28
<211> LENGTH: 7
<212> TYPE: PRT
<213> ORGANISM: ARTIFICIAL
<220> FEATURE:
<223> OTHER INFORMATION: Z2 sequence

<400> SEQUENCE: 28

Glu Glu Ala His Glu Met Lys
1               5

<210> SEQ ID NO 29
<211> LENGTH: 7
<212> TYPE: PRT
<213> ORGANISM: ARTIFICIAL
<220> FEATURE:
<223> OTHER INFORMATION: Z2 sequence

<400> SEQUENCE: 29

Glu Glu Ala His Glu Phe Lys
1               5

<210> SEQ ID NO 30
<211> LENGTH: 7
<212> TYPE: PRT
<213> ORGANISM: ARTIFICIAL
<220> FEATURE:
<223> OTHER INFORMATION: Z2 sequence

<400> SEQUENCE: 30

Glu Glu Ala His Glu Tyr Lys
1               5

<210> SEQ ID NO 31
<211> LENGTH: 15
<212> TYPE: PRT
<213> ORGANISM: ARTIFICIAL
<220> FEATURE:
<223> OTHER INFORMATION: Z2 sequence

<400> SEQUENCE: 31

Glu Glu Ala His Glu Trp Lys Glu Glu Gly Asn Thr Thr Pro Lys
1               5                   10                  15

<210> SEQ ID NO 32
<211> LENGTH: 11
<212> TYPE: PRT
<213> ORGANISM: ARTIFICIAL
```

```
<220> FEATURE:
<223> OTHER INFORMATION: Z2 sequence

<400> SEQUENCE: 32

Glu Glu Leu Asp Ala Arg Leu Glu Ala Leu Lys
1               5                   10

<210> SEQ ID NO 33
<211> LENGTH: 6
<212> TYPE: PRT
<213> ORGANISM: ARTIFICIAL
<220> FEATURE:
<223> OTHER INFORMATION: Z2 sequence

<400> SEQUENCE: 33

Gln Pro Met Tyr Lys Arg
1               5

<210> SEQ ID NO 34
<211> LENGTH: 6
<212> TYPE: PRT
<213> ORGANISM: ARTIFICIAL
<220> FEATURE:
<223> OTHER INFORMATION: Z2 sequence

<400> SEQUENCE: 34

Gly Gln Pro Met Tyr Lys
1               5

<210> SEQ ID NO 35
<211> LENGTH: 6
<212> TYPE: PRT
<213> ORGANISM: ARTIFICIAL
<220> FEATURE:
<223> OTHER INFORMATION: Z2 sequence

<400> SEQUENCE: 35

Pro Gly Gln Pro Met Tyr
1               5

<210> SEQ ID NO 36
<211> LENGTH: 6
<212> TYPE: PRT
<213> ORGANISM: ARTIFICIAL
<220> FEATURE:
<223> OTHER INFORMATION: Z2 sequence

<400> SEQUENCE: 36

Lys Pro Gly Gln Pro Met
1               5

<210> SEQ ID NO 37
<211> LENGTH: 6
<212> TYPE: PRT
<213> ORGANISM: ARTIFICIAL
<220> FEATURE:
<223> OTHER INFORMATION: Z2 sequence

<400> SEQUENCE: 37

Leu Lys Pro Gly Gln Pro
1               5

<210> SEQ ID NO 38
<211> LENGTH: 6
<212> TYPE: PRT
<213> ORGANISM: ARTIFICIAL
<220> FEATURE:
```

-continued

<223> OTHER INFORMATION: Z2 sequence

<400> SEQUENCE: 38

Gln Leu Lys Pro Gly Gln
1               5

<210> SEQ ID NO 39
<211> LENGTH: 6
<212> TYPE: PRT
<213> ORGANISM: ARTIFICIAL
<220> FEATURE:
<223> OTHER INFORMATION: Z2 sequence

<400> SEQUENCE: 39

Leu Gln Leu Lys Pro Gly
1               5

<210> SEQ ID NO 40
<211> LENGTH: 6
<212> TYPE: PRT
<213> ORGANISM: ARTIFICIAL
<220> FEATURE:
<223> OTHER INFORMATION: Z2 sequence

<400> SEQUENCE: 40

Trp Leu Gln Leu Lys Pro
1               5

<210> SEQ ID NO 41
<211> LENGTH: 6
<212> TYPE: PRT
<213> ORGANISM: ARTIFICIAL
<220> FEATURE:
<223> OTHER INFORMATION: Z2 sequence

<400> SEQUENCE: 41

His Trp Leu Gln Leu Lys
1               5

<210> SEQ ID NO 42
<211> LENGTH: 6
<212> TYPE: PRT
<213> ORGANISM: ARTIFICIAL
<220> FEATURE:
<223> OTHER INFORMATION: Z2 sequence

<400> SEQUENCE: 42

Trp His Trp Leu Gln Leu
1               5

<210> SEQ ID NO 43
<211> LENGTH: 6
<212> TYPE: PRT
<213> ORGANISM: ARTIFICIAL
<220> FEATURE:
<223> OTHER INFORMATION: Z2 sequence

<400> SEQUENCE: 43

Ala Trp His Trp Leu Gln
1               5

<210> SEQ ID NO 44
<211> LENGTH: 6
<212> TYPE: PRT
<213> ORGANISM: ARTIFICIAL
<220> FEATURE:
<223> OTHER INFORMATION: Z2 sequence

<400> SEQUENCE: 44

Glu Ala Trp His Trp Leu
1               5

<210> SEQ ID NO 45
<211> LENGTH: 6
<212> TYPE: PRT
<213> ORGANISM: ARTIFICIAL
<220> FEATURE:
<223> OTHER INFORMATION: Z2 sequence

<400> SEQUENCE: 45

Ala Glu Ala Trp His Trp
1               5

<210> SEQ ID NO 46
<211> LENGTH: 6
<212> TYPE: PRT
<213> ORGANISM: ARTIFICIAL
<220> FEATURE:
<223> OTHER INFORMATION: Z2 sequence

<400> SEQUENCE: 46

Glu Ala Glu Ala Trp His
1               5

<210> SEQ ID NO 47
<211> LENGTH: 9
<212> TYPE: PRT
<213> ORGANISM: ARTIFICIAL
<220> FEATURE:
<223> OTHER INFORMATION: Z2 sequence

<400> SEQUENCE: 47

Asp Val Lys Pro Gly Gln Pro Leu Ala
1               5

<210> SEQ ID NO 48
<211> LENGTH: 9
<212> TYPE: PRT
<213> ORGANISM: ARTIFICIAL
<220> FEATURE:
<223> OTHER INFORMATION: Z2 sequence

<400> SEQUENCE: 48

Asp Val Lys Pro Gly Gln Pro Glu Tyr
1               5

<210> SEQ ID NO 49
<211> LENGTH: 9
<212> TYPE: PRT
<213> ORGANISM: ARTIFICIAL
<220> FEATURE:
<223> OTHER INFORMATION: Z2 sequence

<400> SEQUENCE: 49

Asp Val Lys Pro Gly Glu Pro Leu Tyr
1               5

<210> SEQ ID NO 50
<211> LENGTH: 9
<212> TYPE: PRT
<213> ORGANISM: ARTIFICIAL
<220> FEATURE:
<223> OTHER INFORMATION: Z2 sequence

```
<400> SEQUENCE: 50

Asp Val Lys Pro Gly Gln Pro Leu Tyr
1               5

<210> SEQ ID NO 51
<211> LENGTH: 9
<212> TYPE: PRT
<213> ORGANISM: ARTIFICIAL
<220> FEATURE:
<223> OTHER INFORMATION: Z2 sequence

<400> SEQUENCE: 51

Asp Val Lys Pro Gly Gln Pro Leu Glu
1               5

<210> SEQ ID NO 52
<211> LENGTH: 9
<212> TYPE: PRT
<213> ORGANISM: ARTIFICIAL
<220> FEATURE:
<223> OTHER INFORMATION: Z2 sequence

<400> SEQUENCE: 52

Asp Val Lys Pro Gly Gln Pro Met Tyr
1               5

<210> SEQ ID NO 53
<211> LENGTH: 9
<212> TYPE: PRT
<213> ORGANISM: ARTIFICIAL
<220> FEATURE:
<223> OTHER INFORMATION: Z2 sequence

<400> SEQUENCE: 53

Asp Val Lys Pro Gly Gln Glu Leu Tyr
1               5

<210> SEQ ID NO 54
<211> LENGTH: 9
<212> TYPE: PRT
<213> ORGANISM: ARTIFICIAL
<220> FEATURE:
<223> OTHER INFORMATION: Z2 sequence

<400> SEQUENCE: 54

Asp Val Lys Pro Glu Gln Pro Leu Tyr
1               5

<210> SEQ ID NO 55
<211> LENGTH: 9
<212> TYPE: PRT
<213> ORGANISM: ARTIFICIAL
<220> FEATURE:
<223> OTHER INFORMATION: Z2 sequence

<400> SEQUENCE: 55

Asp Val Lys Glu Gly Gln Pro Leu Tyr
1               5

<210> SEQ ID NO 56
<211> LENGTH: 5
<212> TYPE: PRT
<213> ORGANISM: ARTIFICIAL
<220> FEATURE:
<223> OTHER INFORMATION: X5-X4-GDR sequence

<400> SEQUENCE: 56
```

```
Asp Asp Gly Asp Arg
1               5

<210> SEQ ID NO 57
<211> LENGTH: 5
<212> TYPE: PRT
<213> ORGANISM: ARTIFICIAL
<220> FEATURE:
<223> OTHER INFORMATION: X5-X4-GDR sequence

<400> SEQUENCE: 57

Asp Glu Gly Asp Arg
1               5

<210> SEQ ID NO 58
<211> LENGTH: 15
<212> TYPE: PRT
<213> ORGANISM: ARTIFICIAL
<220> FEATURE:
<223> OTHER INFORMATION: N-terminal part of Z1 sequence derived from
      GLP-1(7-37)

<400> SEQUENCE: 58

His Ala Glu Gly Thr Phe Thr Ser Asp Val Ser Ser Tyr Leu Glu
1               5                   10                  15

<210> SEQ ID NO 59
<211> LENGTH: 13
<212> TYPE: PRT
<213> ORGANISM: ARTIFICIAL
<220> FEATURE:
<223> OTHER INFORMATION: N-terminal part of Z1 sequence derived from
      GLP-1(9-37)

<400> SEQUENCE: 59

Glu Gly Thr Phe Thr Ser Asp Val Ser Ser Tyr Leu Glu
1               5                   10

<210> SEQ ID NO 60
<211> LENGTH: 35
<212> TYPE: PRT
<213> ORGANISM: ARTIFICIAL
<220> FEATURE:
<223> OTHER INFORMATION: Enterokinase cleavable polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 60

Xaa Asp Glu Gly Asp Arg Glu Gly Thr Phe Thr Ser Asp Val Ser Ser
1               5                   10                  15

Tyr Leu Glu Gly Gln Ala Ala Lys Glu Phe Ile Ala Trp Leu Val Arg
            20                  25                  30

Gly Arg Gly
        35

<210> SEQ ID NO 61
<211> LENGTH: 35
<212> TYPE: PRT
<213> ORGANISM: ARTIFICIAL
```

```
<220> FEATURE:
<223> OTHER INFORMATION: Enterokinase cleavable polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 61

Xaa Asp Asp Asp Asp Lys Glu Gly Thr Phe Thr Ser Asp Val Ser Ser
1               5                   10                  15

Tyr Leu Glu Gly Gln Ala Ala Lys Glu Phe Ile Ala Trp Leu Val Arg
            20                  25                  30

Gly Arg Gly
        35

<210> SEQ ID NO 62
<211> LENGTH: 43
<212> TYPE: PRT
<213> ORGANISM: ARTIFICIAL
<220> FEATURE:
<223> OTHER INFORMATION: Enterokinase cleavable polypeptide

<400> SEQUENCE: 62

Asp Val Lys Pro Gly Gln Pro Leu Tyr Asp Glu Gly Asp Arg Glu Gly
1               5                   10                  15

Thr Phe Thr Ser Asp Val Ser Ser Tyr Leu Glu Gly Gln Ala Ala Lys
            20                  25                  30

Glu Phe Ile Ala Trp Leu Val Arg Gly Arg Gly
        35                  40

<210> SEQ ID NO 63
<211> LENGTH: 4
<212> TYPE: PRT
<213> ORGANISM: Artificial Sequence
<220> FEATURE:
<223> OTHER INFORMATION: Z2 sequence

<400> SEQUENCE: 63

Glu His Pro Lys
1

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Asp Val Glu Pro Gly Gln Pro Leu Tyr
1               5
```